(12) United States Patent
Tegtmeier et al.

(10) Patent No.: US 8,236,809 B2
(45) Date of Patent: Aug. 7, 2012

(54) SUBSTITUTED 1,2,3-TRIAZOLOPYRIMIDINES FOR THE INHIBITION OF NAD(P)H OXIDASES AND PLATELET ACTIVATION

(75) Inventors: Frank Tegtmeier, Grevenbroich (DE); Ulrich Walter, Veitshöchheim (DE); Reinhard Schinzel, Gerbrunn (DE); Kirstin Wingler, Würzburg (DE); Peter Scheurer, Bergisch Gladbach (DE); Harald Schmidt, Giessen (DE)

(73) Assignee: Vasopharm GmbH (DE)

( * ) Notice: Subject to any disclaimer, the term of this patent is extended or adjusted under 35 U.S.C. 154(b) by 1077 days.

(21) Appl. No.: 11/579,999

(22) PCT Filed: May 13, 2005

(86) PCT No.: PCT/EP2005/005272
§ 371 (c)(1),
(2), (4) Date: Oct. 19, 2007

(87) PCT Pub. No.: WO2005/111041
PCT Pub. Date: Nov. 24, 2005

(65) Prior Publication Data
US 2008/0044354 A1   Feb. 21, 2008

(30) Foreign Application Priority Data
May 18, 2004   (EP) .................................... 04011831

(51) Int. Cl.
C07D 487/04 (2006.01)
A61K 31/519 (2006.01)
A61P 25/28 (2006.01)
A61P 19/02 (2006.01)
A61P 9/00 (2006.01)
A61P 35/00 (2006.01)
A61P 13/12 (2006.01)

(52) U.S. Cl. ..................................... 514/261.1; 544/254
(58) Field of Classification Search .................. 544/254; 514/261.1
See application file for complete search history.

(56) References Cited

U.S. PATENT DOCUMENTS

| | | | |
|---|---|---|---|
| 6,107,300 | A | 8/2000 | Bakthavatchalam et al. |
| 7,045,631 | B2 | 5/2006 | Rosentreter et al. |
| 7,816,350 | B2 | 10/2010 | Fuksova et al. |
| 2005/0004134 | A1 | 1/2005 | Tsutsumi et al. |

FOREIGN PATENT DOCUMENTS

| | | |
|---|---|---|
| JP | 56131586 | 10/1981 |
| JP | 56131587 | 10/1981 |
| JP | 59062594 | 4/1984 |
| JP | 59062595 | 4/1984 |
| WO | 97/35539 A2 | 10/1997 |
| WO | 9901439 | 1/1999 |
| WO | 0136421 A1 | 5/2001 |
| WO | 03/008384 A1 | 1/2003 |
| WO | 03/039451 A2 | 5/2003 |
| WO | 2004005267 A2 | 1/2004 |
| WO | 2004/018473 A2 | 3/2004 |
| WO | 2004037159 A2 | 5/2004 |

OTHER PUBLICATIONS

Vippagunta, S.R., (Adv. Drug. Delivery Rev., 2001, 48, pp. 3-26).*
Shealy et. al. reference (J. Org. Chem., 1961, 26, 4433-4440).*
Alley, Peggy W., J. Org. Chem., 40(12):1837-1838 (1975).
Biagi, G. et al., J. Heterocyclic Chem., 39:885-888 (2002).
Kalai, T. et al, Synthetic Communications, 33(9):1433-1442 (2003).
Sznaidman, Marcos L. and Beauchamp, Lilia M., J. Heterocyclic Chem., 33:1605-1610 (1996).
Office action issued in related Russian Patent Application No. 2006144845, date Feb. 18, 2009.
Betti, Laura et al., "New Amino Derivatives of 1,2,3-Triazolo[4,5-d]Pyrimidines and Their Affinity Towards A1 and A2A Adenosine Receptors," Eur. J. Med. Chem 34 (1999), pp. 867-875.
International Search Report, Application No. PCT/EP2005/005272, dated Feb. 8, 2005.
English translation of Japanese Office Action issued Jun. 9, 2011 in Japanese Patent Application Serial No. 2007-517052.

* cited by examiner

*Primary Examiner* — Susanna Moore
(74) *Attorney, Agent, or Firm* — Michael A. Whittaker; Acuity Law Group, PC

(57) ABSTRACT

The invention relates to compounds of formula het-X-AB containing a N-heteroaryl moiety "het", which is linked via X=sulfur to the 1,2,3-triazolo[4,5-d]pyrimidine-7-yl moiety AB of the formula (II).

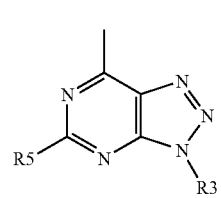

The invention also relates to a process for the preparation of said compounds and the use thereof in drugs for the treatment of NAD(P)H oxidase-related diseases and disorders and inhibition of platelet activation.

6 Claims, No Drawings

SUBSTITUTED 1,2,3-TRIAZOLOPYRIMIDINES FOR THE INHIBITION OF NAD(P)H OXIDASES AND PLATELET ACTIVATION

The invention relates to compounds containing a N-heteroaryl moiety, which is linked via oxygen, sulfur or nitrogen, or via a methylene bridge and oxygen, sulfur or nitrogen to a fused ring moiety, and the use thereof in drugs for the treatment of NAD(P)H oxidases-related diseases and inhibition of platelet activation. In particular, the invention relates to 1,2,3-triazolo[4,5-d]pyrimidine compounds, wherein a N-heteroaryl moiety is linked via oxygen, sulfur or nitrogen, or via a methylene bridge and oxygen, sulfur or nitrogen to the triazolopyrimidinyl moiety. The invention also relates to a process for the preparation of said compounds.

NAD(P)H oxidases (NOX) are multi-subunit enzymes that generate superoxide and other reactive oxygen species (ROS) from oxygen. NAD(P)H oxidases consist of a membrane associated catalytic moiety, the NAD(P)H oxidase homologues, which contain all prosthetic groups needed to transfer electrons from NADPH to oxygen, whereby superoxide is produced. Despite the importance of ROS in the regulation of fundamental physiological processes, ROS production can also cause oxidative stress, which is an important causal factor in the origin and progression of chronic, degenerative diseases such as those of the cardiovascular system. While moderate, physiological concentrations of ROS are regulatory molecules, their production can lead to a variety of defects and miss-regulation if its timing and magnitude is not fine-tuned. An important consequence of the formation of ROS in vascular cells is the consumption of nitric oxide (NO). NO inhibits the development of vascular diseases, and loss of NO is important in the pathogenesis of cardiovascular diseases.

Thus, ROS derived from NAD(P)H oxidases contribute to the pathogenesis of numerous diseases, especially cardiovascular diseases or disorders associated with endothelial dysfunction including but not limited to hypertension, atherosclerosis, cardiac hypertrophy, heart failure, restenosis, diabetes and angina pectoris. Other diseases and disorders associated with an increased NAD(P)H oxidase activity are among others various chronic inflammatory diseases, neurodegenerative diseases including Alzheimer's disease, bronchial asthma, reperfusion injuries, kidney diseases, cancer, arthritis and pulmonary hypertension. In these and other pathological conditions, the NAD(P)H oxidases are a predominant source of ROS, and activation of these enzymes leads to a variety of intracellular signaling events that ultimately cause dysfunction of the endothelium, proliferation of cells, expression of pro-inflammatory genes and reconstruction of the extracellular matrix.

WO 04/005267 A1 discloses substituted heteroaryl and heterocyclic compounds, which are useful in treating or ameliorating a reactive oxygen species (ROS) mediated disease. Said compounds are based on substituted five-membered rings of the heteroazol type.

WO 01/36421 discloses 1,2,3-triazolo[4,5-d]pyrimidine compounds, which are substituted at C-7 with amino groups. Said compounds can act as inhibitors of platelet activation, which is induced by ADP (adenosine 5'-diphosphate). Said compounds have antithrombotic activity.

Further 1,2,3-triazolo[4,5-d]pyrimidine compounds are disclosed in the following documents:

EP 0 201 289 discloses 5-amino-7-halo-1,2,3-triazolo[4,5-d]pyrimidine derivatives with antiviral activity.

JP 59062594 and JP 59062595 disclose 3-phenyl-1,2,3-triazolo[4,5-d]pyrimidine derivatives, which are substituted at C-5 and C-7 with halogen, alkoxy, alkylthio, amino, and which have antitumor activity.

JP 56131586 and JP 56131587 disclose 5H-3-phenyl-1,2,3-triazolo[4,5-d]pyrimidine derivatives, which are substituted at C-7 with cyano, tosyl, alkoxy, phenoxy, hydrazino and the like, which have antitumor activity.

3-[(4-chlorophenyl)methyl]-7-[4-(2-propenyl)-5-(4-pyridinyl)-1,2,4-triazol-3-yl]thio]-1,2,3-triazolo[4,5-d]pyrimidine (Caplus registry number 499140-86-2), 3H-1,2,3-triazolo[4,5-d]pyrimidin-7-amine-3-[(4-fluorophenyl)methyl]-N-2-pyridinyl-(9CI) (Caplus registry number 255370-07-1) and 3H-1,2,3-triazolo[4,5-d]pyrimidin-7-amine-3-[(2-fluorophenyl)methyl]-N2-pyridinyl-(9CI) (Caplus registry number 255369-94-9) are already known.

It was the object of the invention to develop new active agents, which focus on the NO signal cascade and it's counterpart NAD(P)H oxidases (NOX), because NOX inhibitors might have substantial clinical potential for the prevention and treatment of a broad range of diseases and disorders.

This object could be achieved with compounds of the general Formula (I):

$$het\text{-}(CH_2)_n\text{—}X\text{-}AB \quad (I)$$

where
het is five-membered or six-membered N-heteroaryl or fused five-membered or six-membered N-heteroaryl;
n is an integer and is 0 or 1;
X is O, S, $NR_7$ and $R_7$ is selected from $R_3$;
and where the N-atom of the N-heteroaryl moiety and the —$(CH_2)_n$—X group are separated by one carbon atom;
AB is a 1,2,3-triazolo[4,5-d]pyrimidine-7-yl radical of the general Formula (II):

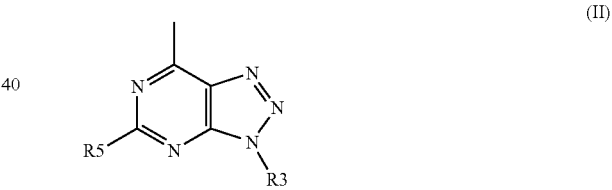

where $R_3$ is hydrogen; alkyl; cycloalkyl; aryl; aralkyl; alkenyl; cyclo-alkenyl; alkynyl; alkyl, cycloalkyl, aryl, aralkyl, alkenyl, cycloalkenyl, alkynyl containing one or more elements selected from the group consisting of O, S, N, halogen (F, Cl, Br, I)
$R_5$ is hydrogen; halogen (F, Cl, Br, I); OH; $R_3$—S; $R_3$—O; $NR_1R_2$, where $R_1$ and $R_2$ are independently from each other $R_3$, or where $R_1$ and $R_2$ form together a ring system; het-$(CH_2)_n$—X, where het, n and X have the meaning as defined above;
or a pharmaceutically acceptable salt or solvate thereof, or a solvate of such a salt;
with the proviso that 3-[(4-chlorophenyl)methyl]-7-[4-(2-propenyl)-5-(4-pyridinyl)-1,2,4-triazol-3-yl]thio]-1,2,3-triazolo[4,5-d]pyrimidine (Caplus registry number 499140-86-2), 3H-1,2,3-triazolo[4,5-d]pyrimidin-7-amine-3-[(4-fluorophenyl)methyl]-N2-pyridinyl-(9CI) (Caplus registry number 255370-07-1) and 3H-1,2,3-triazolo[4,5-d]pyrimidin-7-amine-3-[(2-fluorophenyl)methyl]-N-2-pyridinyl-(9CI) (Caplus registry number 255369-94-9) are excluded.

The term "N-heteroaryl" refers to an aromatic five- or six-membered carbocyclic ring system, wherein at least one carbon atom is substituted by a nitrogen atom. Said term also refers to possible tautomeric forms of said ring system. For example, the 2-hydroxy-pyrimidine system can be written in the form of the tautomeric 1H-2-oxo system.

Said nitrogen atom of the N-heteroaryl moiety and the —$(CH_2)_n$—X group are separated by one carbon atom, what means that the N-heteroaryl moiety is substituted with said group vicinally to said nitrogen atom.

In other embodiments, it is possible to replace further carbon atoms in said N-heteroaryl moiety by further heteroatoms, preferably by nitrogen, oxygen or sulfur atoms.

Preferably, the five-membered N-heteroaryl is imidazolyl, oxazolyl, isoxazolyl, thiazolyl, isothiazolyl, triazolyl, oxdiazolyl, thiadiazolyl, tetrazolyl, oxtriazolyl, thiatriazolyl, which may be substituted with hydrogen and/or with other substituents, preferably those, which are defined below.

In particular preferred are imidazolyl, oxazolyl, thiazolyl.

Preferably, the six-membered N-heteroaryl is pyridinyl, pyrimidinyl, pyrazinyl, pyridazinyl, 1,2,3-triazinyl, 1,2,4-triazinyl, 1,3,5-triazinyl, which may be substituted with hydrogen and/or with other substituents, preferably those, which are defined below.

In particular preferred is pyridinyl, pyrimidinyl.

Furthermore, the N-heteroaryl moiety can be fused with an alicyclic, aromatic or heteroaromatic system, wherein the resulting system may be substituted with hydrogen and/or with other substituents, preferably those, which are defined below.

In one embodiment, the five-membered N-heteroaryl is fused with an aromatic system.

Preferably, said aromatic system is the benzo system. Resulting five-membered N-heteroaryl systems include benzimidazolyl, benzoxazolyl, benzthiazolyl.

Heteroaromatic systems, with which five-membered N-heteroaryl can be fused, are for example, pyridine, quinoline, benzothiazole.

If, for example, the 1,2,4,-trizaole is fused with pyridine, quinoline, benzothiazole, for example, the fused radicals 1,2, 4-triazolo[4,3-a]pyridine-3-yl, 1,2,4-triazolo[4,3-a]quinolin-3-yl and 1,2,4-triazolo[4,3-a]benzothiazol-3-yl can result.

In another embodiment, the six-membered N-heteroaryl is fused with an aromatic system.

Preferably, said aromatic system is the benzo system. Resulting six-membered N-heteroaryl systems include quinolinyl and isoquinolinyl.

Other aromatic systems, with which five- and six membered N-heteroaryl can be fused, include the pyridine and pyrimidine system.

Another aspect of the invention relates to a compound of the general Formula (I), wherein one or more hydrogen atoms of the five-membered or six-membered N-heteroaryl moiety or fused five-membered or six-membered N-heteroaryl moiety can be substituted independently from each other by one or more $R_3$ radicals.

The term "alkyl" refers to a saturated straight or branched carbon chain. Preferably, the chain comprises from 1 to 8 carbon atoms.

The term "cycloalkyl" refers to a saturated monocyclic or bicyclic ring. Preferably, the monocyclic ring system consists of from 3 to 8 carbon atom and the bicyclic ring system of from 9 to 10 carbon atoms. In particular, preferred is a monocyclic ring with from 3 to 6 carbon atoms. Examples are cyclopropyl, cyclobutyl, cyclopentyl or cyclohexyl.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthalenyl or anthracenyl.

The term "aralkyl" refers to an alkyl moiety, which is substituted by aryl, wherein alkyl and aryl have the meaning as outlined above. An example is the benzyl radical.

The terms "alkenyl" and "cycloalkenyl" refer to olefinic unsaturated carbon atoms containing chains or rings with one or more double bonds. Examples are propenyl and cyclohexenyl.

The term "alkynyl" refers to unsaturated carbon atoms containing chains or rings with one or more triple bonds. An example is the propargyl radical.

In one embodiment, carbon atoms or hydrogen atoms in alkyl, cycloalkyl, aryl, aralkyl, alkenyl, cycloalkenyl, alkynyl radicals can be substituted independently from each other with one or more elements selected from the group consisting of O, S, N or with groups containing one or more elements selected from the group consisting of O, S, N.

Embodiments include alkoxy, cycloalkoxy, aryloxy, aralkoxy, alkenyloxy, cycloalkenyloxy, alkynyloxy, alkylthio, cycloalkylthio, arylthio, aralkylthio, alkenylthio, cycloalkenylthio, alkynylthio, alkylamino, cycloalkylamino, arylamino, aralkylamino, alkenylamino, cycloalkenylamino, alkynylamino radicals.

Other embodiments include hydroxyalkyl, hydroxycycloalkyl, hydroxyaryl, hydroxyaralkyl, hydroxyalkenyl, hydroxycycloalkenyl, hydroxyalkynyl, mercaptoalkyl, mercaptocycloalkyl, mercaptoaryl, mercaptoaralkyl, mercaptoalkenyl, mercaptocycloalkenyl, mercaptoalkynyl, aminoalkyl, aminocycloalkyl, aminoaryl, aminoaralkyl, aminoalkenyl, aminocycloalkenyl, aminoalkynyl radicals.

In one embodiment, wherein one or more carbon atom of a carbocyclic system is/are substituted by one or more heteroatoms, a heterocyclyl radical results. The term "heterocyclyl" preferably refers to a saturated or partially unsaturated ring having five members of which at least one member is a N, O or S atom and which optionally contains one additional 0 or one additional N; a saturated or partially unsaturated ring having six members of which at least one member is a N, O or S atom and which optionally contains one additional 0 or one additional N or two additional N atoms; or, a saturated or partially unsaturated bicyclic ring having nine or ten members of which at least one member is a N, O or S atom and which optionally contains one, two or three additional N atoms. Heterocyclyl groups are optionally substituted. Examples include, and are not limited to, pyrrolinyl, pyrrolidinyl, imidazolinyl, imidazolidinyl, pyrazolinyl, pyrazolidinyl, piperidinyl, morpholinyl or piperazinyl.

In another embodiment, hydrogen atoms in alkyl, cycloalkyl, aryl, aralkyl, alkenyl, cycloalkenyl, alkynyl radicals can be substituted independently from each other with one or more halogen atoms. One radical is the trifluoromethyl radical.

If two or more radicals can be selected independently from each other, then the term "independently" means that the radicals may be the same or may be different.

Aspects of the present invention include compounds of the general Formula (I) wherein $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4$), —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Other aspects of the invention include compounds of the Formula (I) wherein substituents of het of the het-(CH$_2$)$_n$—X moiety are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Further aspects of the invention include compounds of the general Formula (I), wherein n is 0 and X is O, S or NR$_7$.

Further aspects of the invention include compounds of the general Formula (I), wherein n is 1 and X is O, S or NR$_7$.

Preferred embodiments of the invention include compounds of the general Formula (I), wherein n is 0 or 1 and X is S.

Other preferred embodiment of the invention include compounds of the general Formula (I), wherein n is 1 and X is O or NR$_7$.

Another aspect of the invention includes compounds of the general Formula (I) wherein R$_3$ is a benzyl radical, which can be substituted. Preferably R$_3$ is CH$_2$-phenyl-R$_4$ and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Still further aspects of the invention include compounds of the general Formula (I) wherein R$_5$ is selected from hydrogen, NH$_2$, (C$_{1-8}$)alkyl, (C$_{3-6}$)cycloalkyl, benzyl, phenyl, preferably from hydrogen, NH$_2$, (C$_{1-8}$)alkyl, benzyl, phenyl.

One aspect of the invention includes compounds of the Formula (I), wherein het is substituted five-membered N-heteroaryl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted five-membered N-heteroaryl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-8}$)alkyl, —O—CO-aryl, —CO—O—(C$_{1-5}$)alkyl, —CO—O-aryl; and n is 0; and X is NR$_7$ and R$_7$ is selected from R$_3$; and R$_3$ and R$_5$ are independently selected from (CO$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted imidazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and $R_3$ and $R_5$ are independently selected from ($C_{0-8}$)alkylene-$R_6$, where $R_6$ is selected from hydrogen, ($C_{1-5}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted imidazolyl, wherein substituents selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is O; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted imidazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is NR$_7$ and $R_7$ is selected from $R_3$; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted oxazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted oxazolyl, wherein substituents selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted oxazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted isoxazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)allyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isoxazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl;

and n is 0; and X is $NR_7$ and $R_7$ is selected from $R_3$; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4)$, —S—$((C_{1-8})$alkyl-$R_4)$, —S—(aryl-$R_4$), —S—(heteroaryl-$R_4$), —S—(heterocyclyl-$R_4$), —S—$((C_{3-6})$cycloalkyl-$R_4)$, $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted thiazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is S; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4)$, —S—$((C_{1-8})$alkyl-$R_4)$, —S—(aryl-$R_4$), —S—(heteroaryl-$R_4$), —S—(heterocyclyl-$R_4$), —S—$((C_{3-6})$cycloalkyl-$R_4)$, $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiazolyl, wherein substituents selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is O; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4)$, —S—$((C_{1-8})$alkyl-$R_4)$, —S—(aryl-$R_4$), —S—(heteroaryl-$R_4$), —S—(heterocyclyl-$R_4$), —S—$((C_{3-6})$cycloalkyl-$R_4)$, $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-8})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is $NR_7$ and $R_7$ is selected from $R_3$; and $R_3$ and $R_5$ are independently selected from $(C_{0-8})$alkylene-$R_6$, where $R_6$ is selected from hydrogen, $(C_{1-8})$alkoxy, —OH, (halogen)-3, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4)$, —S—$((C_{1-8})$alkyl-$R_4)$, —S—(aryl-$R_4$), —S—(heteroaryl-$R_4$), —S—(heterocyclyl-$R_4$), —S—$((C_{3-6})$cycloalkyl-$R_4)$, $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted isothiazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is S; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4)$, —S—$((C_{1-8})$alkyl-$R_4)$, —S—(aryl-$R_4$), —S—(heteroaryl-$R_4$), —S-(heterocyclyl-$R_4$), —S—$((C_{3-6})$cycloalkyl-$R_4)$, $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isothiazolyl, wherein substituents selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isothiazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted triazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted triazolyl, wherein substituents selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted triazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted oxdiazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heterocyclyl-R$_4$), —NH—(heteroaryl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted oxdiazolyl, wherein substituents selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiadiazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-5}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiadiazolyl, wherein substituents selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiadiazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)allyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted tetrazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted tetrazolyl, wherein substituents selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted tetrazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted oxtriazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted oxtriazolyl, wherein substituents selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted thiatriazolyl, wherein substituents are selected independently from each other from hydrogen, —F, —Cl, —OH, —CN, —NO$_2$, —CF$_3$, (C$_{1-8}$) alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiatriazolyl, wherein substituents selected independently from each other from hydrogen, —F, —Cl, —OH, —CN, —NO$_2$, —CF$_3$, (C$_{1-8}$) alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$) alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiatriazolyl, wherein substituents are selected independently from each other from hydrogen, —F, —Cl, —OH, —CN, —NO$_2$, —CF$_3$, (C$_{1-8}$) alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$) alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted five-membered N-heteroaryl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$) alkyl, —CO—O-aryl; and n is 1; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted five-membered N-heteroaryl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)allyl, —O—CO-aryl, —CO—O—(C$_{1-5}$) alkyl, —CO—O-aryl; and n is 1; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)-3, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted five-membered N-heteroaryl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted imidazolyl, wherein substituents are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is S; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted imidazolyl, wherein substituents selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is O; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-R), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is imidazolyl, wherein substituents are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl;

and $R_1$ and $R_2$ are independently selected from H, $(C_1\text{-}C_8)$alkyl, $(C_3\text{-}C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted oxazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is S; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1\text{-}C_8)$alkyl, $(C_3\text{-}C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted oxazolyl, wherein substituents selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is O; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1\text{-}C_8)$alkyl, $(C_3\text{-}C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted oxazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is $NR_7$ and $R_7$ is selected from $R_3$; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1\text{-}C_8)$alkyl, $(C_3\text{-}C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted isoxazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is S; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1\text{-}C_8)$alkyl, $(C_3\text{-}C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isoxazolyl, wherein substituents selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is O; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8})$alkyl-$R_4$), —NH—(aryl-$R_4$), —NH—(heteroaryl-$R_4$), —NH—(heterocyclyl-$R_4$), —NH—(($C_{3-6})$cycloalkyl-$R_4$), —S—(($C_{1-8})$alkyl-$R_4$), —S—(aryl-$R_4$), —S—(heteroaryl-$R_4$), —S-(heterocyclyl-$R_4$), —S—(($C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isoxazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is $NR_7$ and $R_7$ is selected from $R_3$; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8})$alkyl-$R_4$), —NH—(aryl-$R_4$), —NH—(heteroaryl-$R_4$), —NH—(heterocyclyl-$R_4$), —NH—(($C_{3-6})$cycloalkyl-$R_4$), —S—(($C_{1-8})$alkyl-$R_4$), —S—(aryl-$R_4$), —S—(heteroaryl-$R_4$), —S—(heterocyclyl-$R_4$), —S—(($C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted thiazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is S; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8})$alkyl-$R_4$), —NH—(aryl-$R_4$), —NH—(heteroaryl-$R_4$), —NH—(heterocyclyl-$R_4$), —NH—(($C_{3-6})$cycloalkyl-$R_4$), —S—(($C_{1-8})$alkyl-$R_4$), —S—(aryl-$R_4$), —S—(heteroaryl-$R_4$), —S—(heterocyclyl-$R_4$), —S—(($C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiazolyl, wherein substituents selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is O; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8})$alkyl-$R_4$), —NH—(aryl-$R_4$), —NH—(heteroaryl-$R_4$), —NH—(heterocyclyl-$R_4$), —NH—(($C_{3-6})$cycloalkyl-$R_4$), —S—(($C_{1-8})$alkyl-$R_4$), —S—(aryl-$R_4$), —S—(heteroaryl-$R_4$), —S—(heterocyclyl-$R_4$), —S—(($C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is $NR_7$ and $R_7$ is selected from $R_3$; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8})$alkyl-$R_4$), —NH—(aryl-$R_4$), —NH—(heteroaryl-$R_4$), —NH—(heterocyclyl-$R_4$), —NH—(($C_{3-6})$cycloalkyl-R), —S—(($C_{1-8})$alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted isothiazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isothiazolyl, wherein substituents selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and R$_3$ and R$_5$ are independently selected from (C$_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isothiazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-5}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is NR$_7$ and R$_7$ is selected from R$_3$; and R$_3$ and R$_5$ are independently selected from (C$_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted triazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)

alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted triazolyl, wherein substituents selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is O; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —NR$_1$R$_2$, —NH—($(C_{1-8})$alkyl-R$_4$), —NH—(aryl-R$_4$), —NH—(heteroaryl-R$_4$), —NH—(heterocyclyl-R$_4$), —NH—($(C_{3-6})$cycloalkyl-R$_4$), —S—($(C_{1-8})$alkyl-R$_4$), —S—(aryl-R$_4$), —S—(heteroaryl-R$_4$), —S—(heterocyclyl-R$_4$), —S—($(C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted triazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is NR$_7$ and R$_7$ is selected from R$_3$; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —NR$_1$R$_2$, —NH—($(C_{1-8})$alkyl-R$_4$), —NH—(aryl-R$_4$), —NH—(heteroaryl-R$_4$), —NH—(heterocyclyl-R$_4$), —NH—($(C_{3-6})$cycloalkyl-R$_4$), —S—($(C_{1-8})$alkyl-R$_4$), —S—(aryl-R$_4$), —S—(heteroaryl-R$_4$), —S—(heterocyclyl-R$_4$), —S—($(C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted oxdiazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is S; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —NR$_1$R$_2$, —NH—($(C_{1-8})$alkyl-R$_4$), —NH—(aryl-R$_4$), —NH—(heteroaryl-R$_4$), —NH—(heterocyclyl-R$_4$), —NH—($(C_{3-6})$cycloalkyl-R$_4$), —S—($(C_{1-8})$alkyl-R$_4$), —S—(aryl-R$_4$), —S—(heteroaryl-R$_4$), —S—(heterocyclyl-R$_4$), —S—($(C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted oxdiazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is O; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —NR$_1$R$_2$, —NH—($(C_{1-8})$alkyl-R$_4$), —NH—(aryl-R$_4$), —NH—(heteroaryl-R$_4$), —NH—(heterocyclyl-R$_4$), —NH—($(C_{3-6})$cycloalkyl-R$_4$), —S—($(C_{1-8})$alkyl-R$_4$), —S—(aryl-R$_4$), —S—(heteroaryl-R$_4$), —S-(heterocyclyl-R$_4$), —S—($(C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted oxdiazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-8})$alkyl, —S(O)$_2$—$(C_{1-5})$ alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted thiadiazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiadiazolyl, wherein substituents selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiadiazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted tetrazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_9$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted tetrazolyl, wherein substituents selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted tetrazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_1$—S)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted oxtriazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted oxtriazolyl, wherein substituents selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted oxtriazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)-3, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted thiatriazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiatriazolyl, wherein substituents selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted thiatriazolyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted fused five-membered N-heteroaryl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (Co 8)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted fused five-membered N-heteroaryl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is O; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted fused five-membered N-heteroaryl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is NR$_7$ and R$_7$ is selected from R$_3$; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted benzimidazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzimidazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is O; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—

$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzimidazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 0; and X is NR$_7$ and R$_7$ is selected from R$_3$; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1-C_8)$alkyl, $(C_3-C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted benzoxazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 0; and X is S; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1-C_8)$alkyl, $(C_3-C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzoxazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 0; and X is O; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1-C_8)$alkyl, $(C_3-C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzoxazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 0; and X is NR$_7$ and R$_7$ is selected from R$_3$; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1-C_8)$alkyl, $(C_3-C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted benzthiazolyl, wherein substituents are selected independently from each other from hydrogen, —F, —Cl, —OH, —CN, —NO$_2$, —CF$_3$, $(C_{1-8})$ alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is S; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted fused benzthiazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is O; and $R_3$ and $R_5$ are independently selected from (Co 8)alkylene-$R_6$, where $R_6$ is selected from hydrogen, $(C_{1-8})$alkoxy, —OH, (halogen)$_{1-3}$, —$NR_1R_2$, —NH—(($C_{3-6}$)alkyl-$R_4$), —NH—(aryl-$R_4$), —NH—(heteroaryl-$R_4$), —NH—(heterocyclyl-$R_4$), —NH— (($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzthiazolyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is $NR_7$ and $R_7$ is selected from $R_3$; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_9)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted fused five-membered N-heteroaryl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$ alkyl, —CO—O-aryl; and n is 1; and X is S; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted fused five-membered N-heteroaryl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$ alkyl, —CO—O-aryl; and n is 1; and X is O; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl- $R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted fused five-membered N-heteroaryl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is NR$_7$ and R$_7$ is selected from R$_3$; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted benzimidazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzimidazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_9$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzimidazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is NR$_7$ and R$_7$ is selected from R$_3$; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, $(C_1$-$C_8)$alkyl, $(C_3$-$C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted benzoxazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is S; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—$((C_{1-8})$alkyl-R$_4$), —NH—(aryl-R$_4$), —NH—(heteroaryl-R$_4$), —NH—(heterocyclyl-R$_4$), —NH—$((C_{3-6})$cycloalkyl-R$_4$), —S—$((C_{1-8})$alkyl-R$_4$), —S—(aryl-R$_4$), —S—(heteroaryl-R$_4$), —S-(heterocyclyl-R$_4$), —S—$((C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzoxazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is O; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—$((C_{1-8})$alkyl-R$_4$), —NH—(aryl-R$_4$), —NH—(heteroaryl-R$_4$), —NH—(heterocyclyl-R$_4$), —NH—$((C_{3-6})$cycloalkyl-R$_4$), —S—$((C_{1-8})$alkyl-R$_4$), —S—(aryl-R$_4$), —S—(heteroaryl-R$_4$), —S-(heterocyclyl-R$_4$), —S—$((C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzoxazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is NR$_7$ and R$_7$ is selected from R$_3$; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—$((C_{1-8})$alkyl-R$_4$), —NH—(aryl-R$_4$), —NH—(heteroaryl-R$_4$), —NH—(heterocyclyl-R$_4$), —NH—$((C_{3-6})$cycloalkyl-R$_4$), —S—$((C_{1-8})$alkyl-R$_4$), —S—(aryl-R$_4$), —S—(heteroaryl-R$_4$), —S-(heterocyclyl-R$_4$), —S—$((C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted benzthiazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is S; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—$((C_{1-8})$alkyl-R$_4$), —NH—(aryl-R$_4$), —NH—(heteroaryl-R$_4$), —NH—(heterocyclyl-R$_4$), —NH—$((C_{3-6})$cycloalkyl-R$_4$), —S—$((C_{1-8})$alkyl-R$_4$), —S—(aryl-R$_4$), —S—(heteroaryl-R$_4$), —S-(heterocyclyl-R$_4$), —S—$((C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzthiazolyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—($C_{1-5}$)alkyl, —CO—O-aryl; and n is 1; and X is O; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-3}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted benzthiazolyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is NR$_7$ and R$_7$ is selected from R$_3$; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted six-membered N-heteroaryl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted six-membered N-heteroaryl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is O; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted six-membered N-heteroaryl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$) alkyl, —CO—O-aryl; and n is 0; and X is NR$_7$ and R$_7$ is selected from R$_3$; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted pyridinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyridinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyridinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted pyrimidinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyrimidinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyrimidinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted pyridazinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyridazinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyridazinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is NR$_7$ and R$_7$ is selected from R$_3$; and R$_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted 1,2,3-triazinyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,2,3-triazinyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is O; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,2,3-triazinyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is NR$_7$ and R$_7$ is selected from R$_3$; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted 1,2,4-triazinyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—($C_{1-5}$)alkyl, —S(O)$_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,2,4-triazinyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—($C_{1-5}$)alkyl, —S(O)$_2$—$NR_1R_2$, —O—CO—($C_{1-5}$)alkyl, —O—CO-aryl, —CO—O—($C_{1-5}$)alkyl, —CO—O-aryl; and n is 0; and X is O; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-R), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—($C_{1-5}$)alkyl, —S(O)$_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,2,4-triazinyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—($C_{1-5}$)alkyl, —S(O)$_2$—$NR_1R_2$, —O—CO—($C_{1-5}$)alkyl, —O—CO-aryl, —CO—O—($C_{1-5}$)alkyl, —CO—O-aryl; and n is 0; and X is $NR_7$ and $R_7$ is selected from $R_3$; and $R_3$ and $R_5$ are independently selected from ($C_{0-8}$)alkylene-$R_6$, where $R_6$ is selected from hydrogen, ($C_{1-8}$)alkoxy, —OH, (halogen)-3, —$NR_1R_2$, —NH—(($C_{1-8}$ alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—($C_{1-5}$)alkyl, —S(O)$_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted 1,3,5-triazinyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—($C_{1-5}$)alkyl, —S(O)$_2$—$NR_1R_2$, —O—CO—($C_{1-5}$)alkyl, —O—CO-aryl, —CO—O—($C_{1-5}$)alkyl, —CO—O-aryl; and n is 0; and X is S; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—($C_{1-5}$)alkyl, —S(O)$_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,3,5-triazinyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—($C_{1-5}$)alkyl, —S(O)$_2$—$NR_1R_2$, —O—CO—($C_{1-5}$)alkyl, —O—CO-aryl, —CO—O—($C_{1-5}$)alkyl, —CO—O-aryl; and n is 0; and X is O; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—($C_{1-5}$)alkyl, —S(O)$_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,3,5-triazinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted six-membered N-heteroaryl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted six-membered N-heteroaryl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted six-membered N-heteroaryl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted pyridinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$) cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$ alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyridinyl, wherein substituents are selected independently from each other from hydrogen, —F, —Cl, —OH, —CN, —$NO_2$, —$CF_3$, ($C_{1-8}$) alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$) alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is O; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$) cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$) alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyridinyl, wherein substituents are selected independently from each other from hydrogen, —F, —Cl, —OH, —CN, —$NO_2$, —$CF_3$, ($C_{1-8}$) alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$) alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{11}$ g)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted pyrimidinyl, wherein substituents are selected independently from each other from hydrogen, —F, —Cl, —OH, —CN, —$NO_2$, —$CF_3$, ($C_{1-8}$) alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$) alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is S; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$) cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$) alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyrimidinyl, wherein substituents are selected independently from each other from hydrogen, —F, —Cl, —OH, —CN, —$NO_2$, —$CF_3$, ($C_{1-8}$) alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$) alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is O; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$) cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)

alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$) alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyrimidinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted pyridazinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted pyridazinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted 1,2,3-triazinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,2,3-triazinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,2,3-triazinyl, wherein substituents are selected independently from each other from hydrogen, —F, —Cl, —OH, —CN, —NO$_2$, —CF$_3$, (C$_{1-}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted 1,2,4-triazinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,2,4-triazinyl, wherein substituents are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,2,4-triazinyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is NR$_7$ and R$_7$ is selected from R$_3$; and R$_3$ and R$_5$ are independently selected from ($C_{0-8}$)alkylene-R$_6$, where R$_6$ is selected from hydrogen, ($C_{1-8}$)alkoxy, —OH, (halogen)-3, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted 1,3,5-triazinyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,3,5-triazinyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted 1,3,5-triazinyl, wherein substituents are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is NR$_7$ and R$_7$ is selected from R$_3$; and R$_3$ and R$_5$ are independently selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_1$-s)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted fused six-membered N-heteroaryl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is S; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4$), —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted fused six-membered N-heteroaryl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is O; and $R_3$ and $R_5$ are independently selected from $(C_{0-8})$alkylene-$R_6$, where $R_6$ is selected from hydrogen, $(C_{1-8})$alkoxy, —OH, (halogen)-3, —$NR_1R_2$, —NH—$((C_{1-8})$alkyl-$R_4$), —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted fused six-membered N-heteroaryl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is $NR_7$ and $R_7$ is selected from $R_3$; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4$), —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted quinolinyl, wherein substituents are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is S; and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4$), —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_9)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted quinolinyl, wherein substituents, —F, —Cl, —OH, —CN, —$NO_2$, —$CF_3$, $(C_{1-8})$ alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 0; and X is O; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted quinolinyl, wherein substituents of het, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 0; and X is NR$_7$ and R$_7$ is selected from R$_3$; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted isoquinolinyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 0; and X is S; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isoquinolinyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 0; and X is O; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and R$_1$ and R$_2$ are independently selected from H, $(C_1$-$C_8)$alkyl, $(C_3$-$C_6)$cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isoquinolinyl, wherein substituents of het are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 0; and X is NR$_7$ and R$_7$ is selected from R$_3$; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted fused six-membered N-heteroaryl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is S; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted fused six-membered N-heteroaryl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is O; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_9$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted fused six-membered N-heteroaryl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted quinolinyl, wherein substituents are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is S; and $R_3$ and $R_5$ are independently selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl;

and $R_1$ and $R_2$ are independently selected from H, $(C_1-C_8)$ alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted quinolinyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-8})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is O; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8})$alkyl-R$_4$), —NH—(aryl-R$_4$), —NH—(heteroaryl-R$_4$), —NH—(heterocyclyl-R$_4$), —NH—(($C_{3-6})$cycloalkyl-R$_4$), —S—(($C_{1-8})$alkyl-R$_4$), —S—(aryl-R$_4$), —S—(heteroaryl-R$_4$), —S-(heterocyclyl-R$_4$), —S—(($C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted quinolinyl, wherein substituents of het are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is NR$_7$ and R$_7$ is selected from R$_3$; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8})$alkyl-R$_4$), —NH—(aryl-R$_4$), —NH—(heteroaryl-R$_4$), —NH—(heterocyclyl-R$_4$), —NH—(($C_{3-6})$cycloalkyl-R$_4$), —S—(($C_{1-8})$alkyl-R$_4$), —S—(aryl-R$_4$), —S—(heteroaryl-R$_4$), —S—(heterocyclyl-R$_4$), —S—(($C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

One aspect of the invention includes compounds of the Formula (I), wherein het is substituted isoquinolinyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is S; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-5})$alkyl-R$_4$), —NH—(aryl-R$_4$), —NH—(heteroaryl-R$_4$), —NH—(heterocyclyl-R$_4$), —NH—(($C_{3-6})$cycloalkyl-R$_4$), —S—(($C_{1-8})$alkyl-R$_4$), —S—(aryl-R$_4$), —S—(heteroaryl-R$_4$), —S-(heterocyclyl-R$_4$), —S—(($C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isoquinolinyl, wherein substituents are selected independently from each other from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and n is 1; and X is O; and R$_3$ and R$_5$ are independently selected from $(C_{0-8})$alkylene-R$_6$, where R$_6$ is selected from hydrogen, $(C_{1-8})$alkoxy, —OH, (halogen)$_{1-3}$, —NR$_1$R$_2$, —NH—(($C_{1-8})$alkyl-R$_4$), —NH—(aryl-R$_4$), —NH—(heteroaryl-R$_4$), —NH—(heterocyclyl-R$_4$), —NH—(($C_{3-6})$cycloalkyl-R$_4$), —S—(($C_{1-8})$alkyl-R$_4$), —S—(aryl-R$_4$), —S—(heteroaryl-R$_4$), —S-(heterocyclyl-R$_4$), —S—(($C_{3-6})$cycloalkyl-R$_4$), $(C_{1-8})$alkyl-R$_4$, $(C_{3-6})$cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —NR$_1$R$_2$, —CONR$_1$R$_2$, —S—$(C_{1-5})$alkyl, —S(O)$_2$—$(C_{1-5})$alkyl, —S(O)$_2$—NR$_1$R$_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_9)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another aspect of the invention includes compounds of the Formula (I), wherein het is substituted isoquinolinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_3$ and R$_5$ are independently selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_1$-g)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)-3, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$, C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 0; and X is S; and $R_5$ is phenyl; and $R_3$ is selected from ($C_{0-8}$)alkylene-$R_6$, where $R_6$ is selected from hydrogen, ($C_{1-8}$)alkoxy, —OH, (halogen)-3, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted imidazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 0; and X is S; and $R_5$ is H; and $R_3$ is selected from ($C_{0-8}$)alkylene-$R_6$, where $R_6$ is selected from hydrogen, ($C_{1-8}$)alkoxy, —OH, (halogen)-3, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 0; and X is S; and $R_5$ is $NH_2$; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—

($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_5$ is benzyl; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_5$ is phenyl; and R$_3$ is selected from ($C_{0-8}$)alkylene-R$_6$, where R$_6$ is selected from hydrogen, ($C_{1-8}$)alkoxy, —OH, (halogen)-3, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_5$ is H; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_5$ is NH$_2$; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_9$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_5$ is ($C_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 0; and X is S; and $R_5$ is $NH_2$; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 0; and X is S; and $R_5$ is ($C_{1-8}$)alkyl; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 0; and X is S; and $R_5$ is benzyl; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 0; and X is S; and $R_5$ is phenyl; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$) alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$) alkyl, —CO—O-aryl; and n is 0; and X is S; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$) alkyl, —CO—O-aryl; and n is 0; and X is S; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$) alkyl, —CO—O-aryl; and n is 0; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$) alkyl, —CO—O-aryl; and n is 0; and X is S; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted pyridinyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and $R_5$ is H; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 0; and X is S; and $R_5$ is NH$_2$; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$) alkyl, —CO—O-aryl; and n is 0; and X is S; and $R_5$ is benzyl; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1$-$C_8)$alkyl, $(C_3$-$C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is S; and $R_5$ is phenyl; and $R_3$ is selected from $(C_{0-8})$alkylene-$R_6$, where $R_6$ is selected from hydrogen, $(C_{1-8})$alkoxy, —OH, (halogen)-3, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4)$, —S—$((C_{1-8})$alkyl-$R_4)$, —S—(aryl-$R_4$), —S—(heteroaryl-$R_4$), —S—(heterocyclyl-$R_4$), —S—$((C_{3-6})$cycloalkyl-$R_4)$, $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1$-$C_8)$alkyl, $(C_3$-$C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted pyrimidinyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is S; and $R_5$ is H; and $R_3$ is selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4)$, —S—$((C_{1-8})$alkyl-$R_4)$, —S—(aryl-$R_4$), —S—(heteroaryl-$R_4$), —S-(heterocyclyl-$R_4$), —S—$((C_{3-6})$cycloalkyl-$R_4)$, $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$,—$CONR_1R_2$,—S—$(C_{1-5})$alkyl,—$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1$-$C_8)$alkyl, $(C_3$-$C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 0; and X is S; and $R_5$ is $NH_2$; and $R_3$ is selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4)$, —NH—(aryl-$R_4$), —NH—(heteroaryl-$R_4$), —NH—(heterocyclyl-$R_4$), —NH—$((C_{3-6})$cycloalkyl-$R_4)$, —S—$((C_{1-8})$alkyl-$R_4)$, —S—(aryl-$R_4$), —S—(heteroaryl-$R_4$), —S—(heterocyclyl-$R_4$), —S—$((C_{3-6})$cycloalkyl-$R_4)$, $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1$-$C_8)$alkyl, $(C_3$-$C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 57 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 0; and X is S; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl- $R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and $R_5$ is benzyl; and $R_3$ is selected from ($C_{0-8}$)alkylene-$R_6$, where $R_6$ is selected from hydrogen, ($C_{1-8}$)alkoxy, —OH, (halogen)-3, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and $R_5$ is phenyl; and $R_3$ is selected from ($C_{0-8}$)alkylene-$R_6$, where $R_6$ is selected from hydrogen, ($C_{1-8}$)alkoxy, —OH, (halogen)-3, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and $R_5$ is H; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and $R_5$ is NH$_2$; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_9$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-g}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)-3, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and R$_5$ is NH$_2$; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and R$_5$ is ($C_{1-8}$)alkyl; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is S; and R$_5$ is benzyl; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —N—H—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is S; and $R_5$ is phenyl; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted pyridinyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is S; and $R_5$ is H; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is S; and $R_5$ is $NH_2$; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_1$-g)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is S; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)-3, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and R$_5$ is ($C_{1-8}$)alkyl; and R$_3$ is selected from ($C_{0-8}$)alkylene-R$_6$, where R$_6$ is selected from hydrogen, ($C_{1-8}$)alkoxy, —OH, (halogen)-3, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and R$_5$ is benzyl; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and R$_5$ is phenyl; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and R$_5$ is H; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S-(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and R$_5$ is NH$_2$; and R$_3$ is selected from ($C_{0-8}$)alkylene-R$_6$, where R$_6$ is selected from hydrogen, ($C_{1-8}$)alkoxy, —OH, (halogen)-3, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and R$_5$ is ($C_{1-8}$)alkyl; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S-(aryl-R$_4$), —S—(heteroaryl-R$_4$), —S—(heterocyclyl-R$_4$), —S—(($C_{3-6}$)cycloalkyl-R$_4$), ($C_{11}$ g)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and R$_5$ is benzyl; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and $R_5$ is H; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and $R_5$ is NH$_2$; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$) alkyl, —CO—O-aryl; and n is 1; and X is O; and $R_5$ is benzyl; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)-3, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)-3, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl- $R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and $R_5$ is benzyl; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and $R_5$ is phenyl; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted pyridinyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and $R_5$ is H; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S-(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$) alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_1$-$_8$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is O; and $R_5$ is NH$_2$; and $R_3$ is selected from ($C_{0-8}$)alkylene-$R_6$, where $R_6$ is selected from hydrogen, ($C_{1-8}$)alkoxy, —OH, (halogen)$_{1-3}$, —NR$_1$R$_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-8}$)alkyl, —O—CO-aryl, —CO—O—(C$_{1-5}$) alkyl, —CO—O-aryl; and n is 1; and X is O; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$) alkyl, —CO—O-aryl; and n is 1; and X is O; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$) alkyl, —CO—O-aryl; and n is 1; and X is O; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$) alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$) alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is O; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted thiazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is H; and R$_3$ is selected from (C$_{0-8}$)alkylene-R$_6$, where R$_6$ is selected from hydrogen, (C$_{1-8}$)alkoxy, —OH, (halogen)-3, —NR$_1$R$_2$, —NH—((C$_{1-8}$)alkyl-R$_4$), —NH—

(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_5$ is $NH_2$; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_5$ is ($C_{1-8}$)alkyl; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_5$ is benzyl; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted thiazolyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH-(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH-(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted imidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_9$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is benzyl; and R$_3$ is selected from (C$_{0-8}$)alkylene-R$_6$, where R$_6$ is selected from hydrogen, ($C_{1-8}$)alkoxy, —OH, (halogen)$_{1-3}$, —NR$_1$R$_2$, —N—H—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted oxazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is NR$_7$ and R$_7$ is selected from R$_3$; and R$_5$ is phenyl; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is NR$_7$ and R$_7$ is selected from R$_3$; and R$_5$ is H; and R$_3$ is selected from ($C_{0-8}$)alkylene-R$_6$, where R$_6$ is selected from hydrogen, ($C_{1-8}$)alkoxy, —OH, (halogen)-3, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_9$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is NR$_7$ and R$_7$ is selected from R$_3$; and R$_5$ is NH$_2$; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is NR$_7$ and R$_7$ is selected from R$_3$; and R$_5$ is ($C_{1-8}$)alkyl; and R$_3$ is selected from ($C_{0-8}$)alkylene-R$_6$, where R$_6$ is selected from hydrogen, ($C_{1-8}$)alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is $NR_7$ and $R_7$ is selected from $R_3$; and $R_5$ is benzyl; and $R_3$ is selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4$), —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzthiazolyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is $NR_7$ and $R_7$ is selected from $R_3$; and $R_5$ is phenyl; and $R_3$ is selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4$), —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzimidazolyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is $NR_7$ and $R_7$ is selected from $R_3$; and $R_5$ is H; and $R_3$ is selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4$), —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is $NR_7$ and $R_7$ is selected from $R_3$; and $R_5$ is $NH_2$; and $R_3$ is selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—$((C_{1-8})$alkyl-$R_4$), —NH—(aryl-$R_4$), —NH—(heteroaryl-$R_4$), —NH—(heterocyclyl-$R_4$), —NH—$((C_{3-6})$cycloalkyl-$R_4$), —S—$((C_{1-8})$alkyl-$R_4$), —S—(aryl-$R_4$), —S—(heteroaryl-$R_4$), —S—(heterocyclyl-$R_4$), —S—$((C_{3-6})$cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1-C_8)$alkyl, $(C_3-C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S-heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_9$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzimidazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is phenyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from $R_3$; and $R_5$ is $NH_2$; and $R_3$ is selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8}$) alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1$-$C_8)$alkyl, $(C_3$-$C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is $NR_7$ and $R_7$ is selected from $R_3$; and $R_5$ is $(C_{1-8})$alkyl; and $R_3$ is selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8}$) alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1$-$C_8)$alkyl, $(C_3$-$C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$ alkyl, —CO—O-aryl; and n is 1; and is $NR_7$ and $R_7$ is selected from $R_3$; and $R_5$ is benzyl; and $R_3$ is selected from $(C_{0-8})$ alkylene-$R_6$, where $R_6$ is selected from hydrogen, $(C_{1-8})$ alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1$-$C_8)$alkyl, $(C_3$-$C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted benzoxazolyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$ alkyl, —CO—O-aryl; and n is 1; and X is $NR_7$ and $R_7$ is selected from $R_3$; and $R_5$ is phenyl; and $R_3$ is selected from $(C_{0-8})$alkylene-$R_6$, where $R_6$ is selected from hydrogen, $(C_{1-8})$alkoxy, —OH, (halogen)$_{1-3}$, —$NR_1R_2$, —NH—(($C_{1-8}$) alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and $R_1$ and $R_2$ are independently selected from H, $(C_1$-$C_8)$alkyl, $(C_3$-$C_6)$cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted pyridinyl, wherein substituents of het are selected independently from each other from hydrogen, —F, —Cl, —OH, —CN, —$NO_2$, —$CF_3$, $(C_{1-8})$alkyl, $(C_{3-6})$cycloalkyl, heterocyclyl, phenyl, aryl, heteroaryl, $(C_{1-8})$alkoxy, —O-phenyl, —O-aryl, —O-heteroaryl, —$NR_1R_2$, —$CONR_1R_2$, —S—$(C_{1-5})$alkyl, —$S(O)_2$—$(C_{1-5})$alkyl, —$S(O)_2$—$NR_1R_2$, —O—CO—$(C_{1-5})$alkyl, —O—CO-aryl, —CO—O—$(C_{1-5})$alkyl, —CO—O-aryl; and n is 1; and X is $NR_7$ and $R_7$ is selected from $R_3$; and $R_5$ is H; and $R_3$ is selected from $(C_{0-8})$alkylene-$R_6$, where $R_6$ is selected from hydrogen, $(C_{1-8})$alkoxy, —OH, (halogen)-3, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), $(C_{1-8})$alkyl-$R_4$, $(C_{3-6})$cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_5$ is $NH_2$; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_5$ is ($C_{1-8}$)alkyl; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_5$ is benzyl; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyridinyl, wherein substituents of het are selected independently from each other from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_5$ is phenyl; and $R_3$ is selected from ($C_{0-8}$)alkylene-$R_6$, where $R_6$ is selected from hydrogen, ($C_{1-8}$)alkoxy, —OH, (halogen)$_{1-3}$, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —$S(O)_2$—($C_{1-5}$)alkyl, —$S(O)_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

A preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is H; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is NH$_2$; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is (C$_{1-8}$)alkyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and n is 1; and X is NR$_7$ and R$_7$ is selected from R$_3$; and R$_5$ is benzyl; and R$_3$ is selected from (C$_{0-8}$)alkylene-R$_6$, where R$_6$ is selected from hydrogen, (C$_{1-8}$)alkoxy, —OH, (halogen)$_{1-3}$, —NR$_1$R$_2$, —NH—((C$_{1-8}$)alkyl-R$_4$), —NH—(aryl-R$_4$), —NH—(heteroaryl-R$_4$), —NH—(heterocyclyl-R$_4$), —NH—((C$_{3-6}$)cycloalkyl-R$_4$), —S—((C$_{1-8}$)alkyl-R$_4$), —S—(aryl-R$_4$), —S—(heteroaryl-R$_4$), —S—(heterocyclyl-R$_4$), —S—((C$_{3-6}$)cycloalkyl-R$_4$), (C$_{1-8}$)alkyl-R$_4$, (C$_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—(C$_{1-5}$)alkyl, —O—CO-aryl, —CO—O—(C$_{1-5}$)alkyl, —CO—O-aryl; and R$_1$ and R$_2$ are independently selected from H, (C$_1$-C$_8$)alkyl, (C$_3$-C$_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Another preferred embodiment of the invention includes compounds of the Formula (I), wherein het is substituted pyrimidinyl, wherein substituents of het are selected independently from each other from hydrogen, —F, —Cl, —OH, —CN, —NO$_2$, —CF$_3$, (C$_{1-8}$)alkyl, (C$_{3-6}$)cycloalkyl, heterocyclyl, phenyl, aryl, heteroaryl, (C$_{1-8}$)alkoxy, —O-phenyl, —O-aryl, —O-heteroaryl, —NR$_1$R$_2$, —CONR$_1$R$_2$, —S—(C$_{1-5}$)alkyl, —S(O)$_2$—(C$_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and n is 1; and X is $NR_7$ and $R_7$ is selected from $R_3$; and $R_5$ is phenyl; and $R_3$ is selected from ($C_{0-8}$)alkylene-$R_6$, where $R_6$ is selected from hydrogen, ($C_{1-8}$)alkoxy, —OH, (halogen)-3, —$NR_1R_2$, —NH—(($C_{1-8}$)alkyl-$R_4$), —NH—(aryl-$R_4$), —NH—(heteroaryl-$R_4$), —NH—(heterocyclyl-$R_4$), —NH—(($C_{3-6}$)cycloalkyl-$R_4$), —S—(($C_{1-8}$)alkyl-$R_4$), —S—(aryl-$R_4$), —S—(heteroaryl-$R_4$), —S—(heterocyclyl-$R_4$), —S—(($C_{3-6}$)cycloalkyl-$R_4$), ($C_{1-8}$)alkyl-$R_4$, ($C_{3-6}$)cycloalkyl-$R_4$, heterocyclyl-$R_4$, phenyl-$R_4$, aryl-$R_4$, heteroaryl-$R_4$, and $R_4$ is from 1 to 3 substituents independently selected from hydrogen, —F, —Cl, —OH, —CN, —$NO_2$, —$CF_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —$NR_1R_2$, —$CONR_1R_2$, —S—($C_{1-5}$)alkyl, —S(O)$_2$—($C_{1-5}$)alkyl, —S(O)$_2$—$NR_1R_2$, —O—CO—($C_{1-5}$)alkyl, —O—CO-aryl, —CO—O—($C_{1-5}$)alkyl, —CO—O-aryl; and $R_1$ and $R_2$ are independently selected from H, ($C_1$-$C_8$)alkyl, ($C_3$-$C_6$)cycloalkyl, phenyl, aryl, or where $R_1$ and $R_2$ form together a saturated, partially unsaturated or unsaturated carbon chain, which contains from 3 to 7 carbon atoms, wherein at least one carbon atom can be replaced by O, S or N.

Furthermore, one or some of the crystalline form(s) for the compound of the general Formula (I) may exist as polymorphs. Such forms are intended to be included in the present invention. In addition, some of the compounds may form solvates with water (i.e., hydrates) or with common organic solvents, and such solvates are also intended to be encompassed within the scope of this invention.

Still another object of the invention is a process for the manufacture of a compound of the general Formula (I), wherein a compound of the general Formula (III) is reacted with a compound of the general Formula (IV):

het-(CH$_2$)$_n$—X—H    (III)

Y-AB    (IV)

wherein het-(CH$_2$)$_n$—X and AB have the meaning as defined above, H is a hydrogen atom and Y is a nucleofuge.

Preferably, Y is halogen or an organic sulfonate radical.
Preferably, the halogen is chlorine or bromine.
Preferred sulfonate radicals include the methansulfonate, p-methylphenyl-sulfonate or the trifluormethylsulfonate radical.

The reaction of the compound of the general Formula (III) with a compound of the general Formula (IV) can be carried out according to procedures, which are common in the field of organic chemistry.

Preferably, the reaction is carried out using a solvent, wherein the compound of the general Formula (III) and the compound of the general Formula (IV) are preferably at least partially soluble. Suitable solvents are polar, unpolar, protic and aprotic organic solvents, inter alia, chlorohydrocarbons having up to three C atoms such as methylene chloride, nitrites such as acetonitrile, esters such as ethyl acetate, ketones such as methyl ethyl ketone or acetone, open-chain or cyclic ethers such as THF or dioxane or aromatic compounds such as toluene or xylenes, formamides such as dimethylformamide, sulfoxides such as dimethylsulfoxide, ethers such as diethylether, hydrocarbons such as hexane or cyclohexane, or mixtures of two or more of these solvents.

If the compounds have a reduced solubility, phase transfer catalysts can be applied.

The reaction can be carried out within a broad temperature range. A range of from −20° C. to reflux temperature of the solvent can be applied.

During the reaction of the compound of the general Formula (III) and the compound of the general Formula (IV) an acid HY is formed. Dependent from the nucleofuge, said acid is hydrogen halogenide or a sulfonic acid. In order to increase the reaction rate, preferably said acid is neutralized with a base. Bases are for example sodium carbonate, sodium hydrogencarbonate, triethylamine, and the like. By using said base, during the reaction a salt from the base to be applied and the nucleofuge is formed. Mostly, said salt is insoluble in the solvent and precipitates.

Mostly, the target compound is soluble in the solvent. Then, said salt is removed by filtration or by extracting with water. The solvent is removed and the crude solid target compound can be cleaned for example by re-crystallization or by the common chromatographic methods.

If the target compound is insoluble in the solvent, it is preferably isolated by filtration, whereby inorganic or organic salts are removed by extraction with water, and subsequently the residue is cleaned as described above.

The compounds of the general Formula (III) are known or can be prepared according to known methods or by modifying literature preparations.

The compounds of the general Formula (IV) are also known or can be prepared according to known methods or by modifying literature preparations.

Examples for monocyclic compounds of the general Formula (III), wherein n is 0 (het-X—H) are 2-mercaptothiazole, which can be prepared by reaction of the corresponding bromo derivative with thiourea in refluxing methanol (Biagi, G, Giorgi, I., Livi, O., Pacchini, F., Scartoni, V. J. Heterocycle Chem. 2002, 39, 885); or the oxazole derivative, which can be prepared from acetonitrile glyoxaldehyde dimer by reaction with thiocyanic acid (WO 03/006442).

Examples for benzo-fused compounds of the general Formula (III), wherein n is 0 (het-X—H) are the commercial available 2-mercaptopyridine, 2-mercaptobenzoxazole and 2-mercaptoimidazole. For example, 2-mercapto-benzimidazole can be prepared by reaction of aniline, carbondisulfide and sulfur (CAS registry number 149-30-4).

An example for a monocyclic compound of the general Formula (III), wherein n is 1 (het-CH$_2$—X—H) is 2-hydroxymethylene-imidazole, which can be prepared by reaction of imidazole with formaldehyde (Journal of Organic Chemistry, 40 (12), 1837-8; 1975).

An example for a benzo-fused compound of the general Formula (III), wherein n is 1 (het-CH$_2$—X—H) is 2-mercaptomethylene-benzothiazole, which can be prepared by reaction of 2-chloromethylene-benzothiazole with sodium thiocarbonate (Synthetic Communication, 33 (9), 1433-1442; 2003).

The compounds of the general Formula (IV) are also known or can be prepared according to known methods or by modifying literature preparations.

For example, a triazolopyrimidine of the general Formula (IV) with a benzyl radical for $R_3$ and a hydrogen atom for $R_5$, in which Y is chloride, can be prepared by the following common procedure: benzyl bromide is reacted with sodium azide in DMSO at room temperature to give the azide. The azide, which can be used as the crude, is reacted with cyanoacetamide and sodium ethoxide in refluxing ethanol to obtain 4-formamido-5-amino-1-benzylamino-1,2,3-triazole, which can be isolated or reacted in situ with ethyl formiate to form the triazolopyrimidine. Subsequent reaction with thionyl chloride gives the chlorine compound. Such products are disclosed in the documents of the prior art.

Compounds of the general Formula (IV) substituted by e.g. a methyl or phenyl radical for $R_5$ can be obtained using the same reaction procedure as described above. Using the ethylesters of acetic acid or benzoic acid instead of ethyl formiate conducts to the corresponding triazolopyrimidine compounds.

Another example is the synthesis of compounds of the general Formula (IV) with an amino group for $R_5$. The synthesis of said amino derivatives has been reported in literature (Sznaidman, M. L., Beauchamp, L. M., J. Heterocyclic Chem. 1996, 33, 1605-1610). 2-amino-4,6-dichloro-pyrimidine is nitrated yielding the 5-nitro derivative. The nitrodichloropyrimidine reacts very rapidly with amines, whereby one chloro atom can be substituted selectively. For example, by reaction with benzylamine the corresponding 2-amino-4-benzylamino-6-chloro-5-nitro-pyrimidine can be prepared. Subsequently, the nitro group is reduced, for example by means of iron in acetic acid. Then, the amino group is diazotated, conducting to the triazolopyrimidine scaffold.

Yet another synthesis for compounds of the general Formula (IV) with hydrogen for $R_5$ is outlined in the following: starting from commercially available 4,6-dihydroxy-pyrimidine, the dichloro derivative thereof can be obtained by reaction with $POCl_3$. Subsequently, said compound is nitrated yielding the 5-nitro derivative thereof. 4,6-dichloro-5-nitro-pyrimidine reacts very rapidly with amines, whereby one chloro atom can be substituted selectively. For example, by reaction with p-methoxybenzylamine, phenylamine and o-chlorobenzylamine, the corresponding 4-amino-substituted-6-chloro-5-nitro-pyrimidine can be prepared. Subsequently, the nitro group is reduced, for example by means of iron in acetic acid. Then, the amino group is diazotated, conducting to the triazolopyrimidine scaffold.

1,2,3-triazolo-[4,5-d]pyrimidine compounds with amino, thio and oxy substituents for $R_5$ can be prepared from the corresponding halogen-substituted compounds by substitution reaction with appropriate amines, thiols, or oxy compounds, whereby halogen is eliminated. Starting material can be the 5-halo-1,2,3-triazolo-[4,5-d]pyrimidines as disclosed in the documents of the prior art.

An embodiment of the present invention includes the use of a compound of the Formula (I) for the preparation of a pharmaceutical composition or drug thereof for treating or ameliorating a reactive oxygen species mediated and NAD(P)H oxidases-related disease or disorder in a subject in need thereof.

A NAD(P)H oxidases-related disorder includes cardiovascular diseases and disorders including, but is not limited to, hypertension, atherosclerosis, cardiac hypertrophy, heart failure, restenosis, diabetes, and angina pectoris. In addition, other diseases and disorders coinciding with increased NAD (P)H oxidases-mediated superoxide production include, but are not limited to, arthritis, chronic inflammatory bowel diseases (IBD), sepsis and other inflammatory disorders, bronchial asthma, chronic obstructive pulmonary disease (COPD), Acute Respiratory Distress Syndrome (ARDS), cancer, auto-immune diseases, reperfusion injuries, kidney diseases, stroke, Alzheimer's disease, Parkinson's disease and other neurodegenerative diseases, cystic fibrosis, organ rejections, and pulmonary hypertension.

A reactive oxygen species (ROS) mediated inflammatory disorder also includes, and is not limited to, phosphorylation mediated disorders, polymorphonuclear leucocyte mediated disorders, macrophage mediated disorders, lipopolysaccharide mediated disorders, tumor necrosis factor-α mediated disorders, cytokine IFN-γ mediated disorders, interleukin-2 mediated disorders, inflanmnatory arthritis, potassium peroxochromate arthritis, rheumatoid arthritis, osteoarthritis or Alzheimer's disease.

An embodiment of the present invention includes a method for treating or ameliorating a reactive oxygen species (ROS) mediated and NAD(P)H oxidases (NOX)-related disease disorder in a subject in need thereof comprising administering to the subject a therapeutically effective amount of an instant compound of the general Formula (I) or pharmaceutical composition thereof.

In a method for treating or ameliorating said reactive oxygen species (ROS) mediated disorder, the term "reactive oxygen species" includes, and is not limited to, a reactive oxygen species selected from a superoxide, hydrogen peroxide, hydroxyl radical or HOCl reactive oxygen species.

Moreover, it was found that the compound of the general Formula (I) can inhibit the platelet activation. Said inhibition may be dependent or independent from the NOX inhibition.

Preferably, said inhibition is the inhibition of thrombin-induced platelet activation.

It is apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation and the advancement of the disease condition. In addition, factors associated with the particular subject being treated, including subject age, weight, diet and time of administration, will result in the need to adjust the dose to an appropriate therapeutic level.

A therapeutically effective amount for use of the instant compounds or a pharmaceutical composition thereof comprises a dose range of from about 0.001 mg to about 2,000 mg, a dose range of from about 0.1 mg to about 500 mg or a dose range of from about 1 mg to about 250 mg of active ingredient per day for an average (70 kg) human.

For oral administration, a pharmaceutical composition is preferably provided in the form of tablets containing, 0.01, 0.05, 0.1, 1.0, 2.5, 5.0, 10.0, 15.0, 25.0, 50.0, 100, 150, 250 and 500 milligrams of the active ingredient for the symptomatic adjustment of the dosage to the subject to be treated.

If the compounds of the invention or a pharmaceutical composition containing the compounds of the invention is tested in a test animal, preferably a rodent, in particular a rat, then preferably an effective amount of active ingredient of preferably from 0.014 mg to 3.5 mg is applied to said average (500 g) test animal Surprisingly, it was found that not only compounds of the general Formula (I) with the specific 1,2,3-triazolo[4,5-d] pyrimidine-7-yl moiety of the Formula (II) as disclosed above advantageously inhibit NOX and/or the platelet activation.

Also compounds with AB moieties related to the 1,2,3-triazolo[4,5-d]pyrimidine-7-yl moiety can show said advantageous behavior.

Said compounds have the general Formula (V):

$$het\text{-}(CH_2)_n\text{---}X\text{-}AB \qquad (V)$$

where
het is five-membered or six-membered N-heteroaryl or fused five-membered or six-membered N-heteroaryl;
n is an integer and is 0 or 1;
X is O, S, $NR_7$ and $R_7$ is selected from $R_3$;
and where the N-atom of the N-heteroaryl moiety and the —$(CH_2)_n$—X group are separated by one carbon atom;
A is aryl or heteroaryl;
B is a moiety containing a five-membered ring, where said ring is fused with A;
$R_3$ is hydrogen; alkyl; cycloalkyl; aryl; aralkyl; alkenyl; cycloalkenyl; alkynyl; alkyl, cycloalkyl, aryl, aralkyl, alkenyl, cycloalkenyl, alkynyl containing one or more elements selected from the group consisting of O, S, N, halogen (F, Cl, Br, I); or a pharmaceutically acceptable salt or solvate thereof, or a solvate of such a salt.

The term "N-heteroaryl" refers to an aromatic five- or six-membered carbocyclic ring system, wherein at least one carbon atom is substituted by a nitrogen atom. Said term also refers to tautomeric forms of said ring system. For example, the 2-hydroxy-pyrimidine system can be written in the form of the tautomeric 1H-2-oxo system.

Said N-atom of the N-heteroaryl moiety and the —$(CH_2)_n$—X group are separated by one carbon atom, what means that the N-heteroaryl moiety is substituted with said group vicinally to said nitrogen atom.

In other embodiments, it is possible replacing further carbon atoms in said N-heteroaryl moiety by further heteroatoms, preferably by nitrogen, oxygen or sulfur atoms.

Preferably, the five-membered N-heteroaryl is imidazolyl, oxazolyl, isoxazolyl, thiazolyl, isothiazolyl, triazolyl, oxdiazolyl, thiadiazolyl, tetrazolyl, oxtriazolyl, thiatriazolyl, which may be substituted with hydrogen and/or with other substituents, preferably those, which are defined below.

In particular preferred are imidazolyl, oxazolyl, thiazolyl.

Preferably, the six-membered N-heteroaryl is pyridinyl, pyrimidinyl, pyrazinyl, pyridazinyl, 1,2,3-triazinyl, 1,2,4-triazinyl, 1,3,5-triazinyl, which may be substituted with hydrogen and/or with other substituents, preferably those, which are defined below.

In particular preferred is pyridinyl, pyrimidinyl.

Furthermore, the N-heteroaryl moiety can be fused with an alicyclic, aromatic or heteroaromatic system, wherein the resulting fused system may be substituted with hydrogen and/or with other substituents, preferably those, which are defined below.

In one embodiment, the five-membered N-heteroaryl is fused with an aromatic system.

Preferably, said aromatic system is the benzo system. Resulting five-membered N-heteroaryl systems include benzimidazolyl, benzoxazolyl, benzthiazolyl, which may be substituted with hydrogen and/or with other substituents, preferably those, which are defined below.

If, for example, the 1,2,4,-trizaole is fused with pyridine, quinoline, benzothiazole, for example, the fused radicals 1,2,4-triazolo[4,3-a]pyridine-3-yl, 1,2,4-triazolo[4,3-a]quinolin-3-yl and 1,2,4-triazolo[4,3-a]benzothiazol-3-yl can result.

In another embodiment, the six-membered N-heteroaryl is fused with an aromatic system.

Preferably, said aromatic system is the benzo system. Resulting six-membered N-heteroaryl systems include quinolinyl and isoquinolinyl.

Other aromatic systems, with which five- and six membered N-heteroaryl can be fused, include the pyridine and pyrimidine system.

Another aspect of the invention relates to a compound of the general Formula (V), wherein one or more hydrogen atoms of the five-membered or six-membered N-heteroaryl moiety or fused five-membered or six-membered N-heteroaryl moiety can be substituted independently from each other by one or more $R_3$ radicals.

In the general Formula (V) A stands for aryl or heteroaryl, what means that A is preferably phenyl, naphthenyl, anthracenyl, or phenyl, naphthenyl, anthracenyl containing one or more heteroatoms selected from the group consisting of N, O, S. The five-membered ring of the B moiety is a carbocyclic or heterocyclic ring. Preferably said ring contains one or more heteroatoms selected from the group consisting of N, O, S.

Another aspect of the invention includes a compound of the general Formula (V), wherein the AB moiety is substituted with one or more radicals selected from $R_3$ and $R_5$, where $R_3$ is hydrogen; alkyl; cycloalkyl; aryl; aralkyl; alkenyl; cycloalkenyl; alkynyl; alkyl, cycloalkyl, aryl, aralkyl, alkenyl, cycloalkenyl, alkynyl containing one or more elements selected from the group consisting of O, S, N, halogen (F, Cl, Br, I); and $R_5$ is hydrogen; halogen (F, Cl, Br, I); OH; $R_3$—S; $R_3$—O; $NR_1R_2$, where $R_1$ and $R_2$ are independently from each other $R_3$, or where $R_1$ and $R_2$ form together a ring system; het-$(CH_2)_n$—X, where het, n and X have the meaning as defined above.

Examples for the AB moiety are the following moieties (Caplus registry numbers of exemplified compounds containing said moieties):

2,1,3-benzoxadiazol-4-yl (662162-64-3); 5H-cyclopenta[4,5]thieno[2,3-d]pyrimidin-6-yl (571918-81-5); thieno[2,3-d]pyrimidin-4-yl (561010-33-1); pyrido[1,2-a]benzimidazol-1-yl (571149-57-0); benzothieno[2,3-d]pyrimidin-4-yl (556018-82-7); 5H-cyclopenta[4,5]thieno[2,3-d]pyrimidin-4-yl (556018-16-7); 1,3-imidazolo[4,5-d]pyrimidin-4-yl (664325-10-4); 1,2,4-triazolo[4,3-a]quinolinyl (556018-7); 1H-indol-7-yl (548458-07-7); 1,3-dihydro-2H-2-oxo-benzimidazol-yl (548457-72-3); 1,2,4-triazolo[1,5-a]pyrimidin-7-yl (501916-02-5); pyrido[3',2':4,5]thieno[2,3-d]pyrimidin-4-yl (499140-77-1); 1H-pyrazolo[3,4-d]pyrimidin-4-yl (496971-16-5); 1H-purin-6-yl (477280-92-5); 1H-pyrrolo[2,3-d]pyrimidin-4-yl (417721-57-4); purin-6-yl (409304-31-0, 397885-88-0); imidazo[1,2-c]pyrimidin-5-yl (371169-97-0); benzofuro[3,2-d]pyrimidin-4-yl (354130-21-5); 2,1,3-benzothiadiazol-7-yl (352347-99-0); naphth[2,1-d]-1,3-oxathiol-2-oxo-4-yl (348579-51-1); thiazolo[4,5-d]pyrimidin-7-yl (309735-15-7); 1H-pyrrolo[3,4-c]pyridin-4-yl (309735-15-7); 1,2,4-triazolo[4,3-a]quinoxalin-4-yl (223926-34-9); 1,2,4-triazolo[1,5-a]pyridin-5-yl (179098-91-0); pyrazolo[1,5-a]pyrimidin-7-yl (174668-50-9); 1,2,4-triazolo[1,5-a]pyrimidin-7-yl (174668-48-5); pyrido[1,2-a]benzimidazol-1-yl (612523-67-8); 1-indolizin-8-yl (622836-49-1); 1H-indol-4-yl (477856-99-8); benzo[b]thiophen-7-yl (475480-73-0); benzofuran-4-yl (475480-56-9); thieno[3,2-b]pyridin-7-yl (385783-90-4); imidazo[5,1-a]isoquinolin-5-yl (376356-45-6); pyrido[3,2-e]-1,2,4-triazolo[4,3-a]pyrazin-6-yl (308104-62-3); 9H-carbazol-5-yl (220862-74-8); 2,3,4,9-tetrahydro-1H-carbazol-5-yl (207340-78-1); isoxazolo[5,4-d]pyrimidin-4-yl (141564-88-7); 1H-pyrazolo[3,4-d]pyrimidin-4-yl (393822-77-0).

The term "alkyl" refers to a saturated straight or branched carbon chain. Preferably, the chain comprises from 1 to 8 carbon atoms.

The term "cycloalkyl" refers to a saturated monocyclic or bicyclic ring. Preferably, the monocyclic ring system consists of from 3 to 8 carbon atom and the bicyclic ring system of from 9 to 10 carbon atoms. In particular preferred is a monocyclic ring with from three to six carbon atoms. Examples are cyclopropyl, cyclobutyl, cyclopentyl or cyclohexyl.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthalenyl or anthracenyl.

The term "aralky" refers to an alkyl moiety, which is substituted by aryl, wherein alkyl and aryl have the meaning as outlined above. An example is the benzyl radical.

The terms "alkenyl" and "cycloalkenyl" refer to olefinic unsaturated carbon atoms-containing chains or rings with one or more double bonds. Examples are propenyl and cyclohexyl.

The term "alkynyl" refers to unsaturated carbon atoms containing chains or rings with one or more triple bonds. An example is the propargyl radical.

In one embodiment, carbon atoms or hydrogen atoms in alkyl, cycloalkyl, aryl, aralkyl, alkenyl, cycloalkenyl, alkynyl radicals can be substituted independently from each other with one or more elements selected from the group consisting of O, S, N or with groups containing one or more elements selected from the group consisting of O, S, N.

Embodiments include alkoxy, cycloalkoxy, aryloxy, aralkoxy, alkenyloxy, cycloalkenyloxy, alkynyloxy, alkylthio, cycloalkylthio, arylthio, aralkylthio, alkenylthio, cycloalkenylthio, alkynylthio, alkylamino, cycloalkylamino, arylamino, aralkylamino, alkenylamino, cycloalkenylamino, alkynylamino radicals.

Other embodiments include hydroxyalkyl, hydroxycloalkyl, hydroxyaryl, hydroxyaralkyl, hydroxyalkenyl, hydroxycycloalkenyl, hydroxyalkynyl, mercaptoalkyl, mercaptocycloalkyl, mercaptoaryl, mercaptoaralkyl, mercaptoalkenyl, mercaptocycloalkenyl, mercaptoalkynyl, aminoalkyl, aminocycloalkyl, aminoaryl, aminoaralkyl, aminoalkenyl, aminocycloalkenyl, aminoalkynyl radicals.

In one embodiment, wherein one or more carbon atom of a carbocyclic system is/are substituted by one or more heteroatoms, a heterocyclyl radical results. The term "heterocyclyl" preferabyl refers to a saturated or partially unsaturated ring having five members of which at least one member is a N, O or S atom and which optionally contains one additional O or one additional N; a saturated or partially unsaturated ring having six members of which at least one member is a N, O or S atom and which optionally contains one additional O or one additional N or two additional N atoms; or, a saturated or partially unsaturated bicyclic ring having nine or ten members of which at least one member is a N, O or S atom and which optionally contains one, two or three additional N atoms. Heterocyclyl groups are optionally substituted. Examples include, and are not limited to, pyrrolinyl, pyrrolidinyl, imidazolinyl, imidazolidinyl, pyrazolinyl, pyrazolidinyl, piperidinyl, morpholinyl or piperazinyl.

In another embodiment, hydrogen atoms in alkyl, cycloalkyl, aryl, aralkyl, alkenyl, cycloalkenyl, alkynyl radicals can be substituted independently from each other with one or more halogen atoms. One radical is the trifluoromethyl radical.

If two or more radicals can be selected independently from each other, then the term "independently" means that the radicals may be the same or may be different.

Aspects include compounds of the general Formula (V) wherein the AB moiety can be substituted with one or more radicals selected from $R_3$ and $R_5$, and $R_3$ and $R_5$ are independently selected from $(C_{0-8})$alkylene-$R_6$, where $R_6$ is selected from hydrogen, $(C_{1-8})$alkoxy, —OH, (halogen)$_{1-3}$, —NR$_1$R$_2$, —NH—(($C_{1-8}$)alkyl-R$_4$), —NH—(aryl-R$_4$), —NH—(heteroaryl-R$_4$), —NH—(heterocyclyl-R$_4$), —NH—(($C_{3-6}$)cycloalkyl-R$_4$), —S—(($C_{1-8}$)alkyl-R$_4$), —S—(aryl-R$_4$), —S—(heteroaryl-R$_4$), —S—(heterocyclyl-R$_4$), —S—(($C_{3-6}$)cycloalkyl-R$_4$), ($C_{1-8}$)alkyl-R$_4$, ($C_{3-6}$)cycloalkyl-R$_4$, heterocyclyl-R$_4$, phenyl-R$_4$, aryl-R$_4$, heteroaryl-R$_4$, and R$_4$ is from 1 to 3 substituents independently selected from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Other aspects of the invention include compounds of the Formula (V) wherein substituents of het of the het-(CH$_2$)$_2$—X moiety are selected independently from each other from hydrogen, —F, —Cl, —OH, —CN, —NO$_2$, —CF$_3$, ($C_{1-8}$)alkyl, ($C_{3-6}$)cycloalkyl, heterocyclyl, phenyl, aryl, heteroaryl, ($C_{1-8}$)alkoxy, —O-phenyl, —O-aryl, —O-heteroaryl, —NR$_1$R$_2$, —CONR$_1$R$_2$, —S—($C_{1-5}$)alkyl, —S(O)$_2$—($C_{1-5}$)alkyl, —S(O)$_2$—NR$_1$R$_2$, —O—CO—($C_{1-5}$)alkyl, —O—CO-aryl, —CO—O—($C_{1-5}$)alkyl, —CO—O-aryl; and R$_1$ and R$_2$ are independently selected from H, ($C_1$-$C_8$)alkyl, ($C_3$-$C_6$)cycloalkyl, phenyl, aryl, or where R$_1$ and R$_2$ form together a saturated, partially unsaturated or unsaturated carbon chain, which contains from 3 to 7 carbon atoms, wherein at least one carbon atom can be replaced by O, S or N.

Further aspects of the invention include compounds of the general Formula (V), wherein n is 0 and X is O, S or NR$_7$.

Further aspects of the invention include compounds of the general Formula (V), wherein n is 1 and X is O, S or NR$_7$.

Preferred embodiments of the invention include compounds of the general Formula (I), wherein n is 0 or 1 and X is S.

Other preferred embodiments of the invention include compounds of the general Formula (I), wherein n is 1 and X is O or NR$_7$.

Furthermore, one or some of the crystalline form(s) for the compound of the general Formula (V) may exist as polymorphs. Such forms are intended to be included in the present invention. In addition, some of the compounds may form solvates with water (i.e., hydrates) or with common organic solvents, and such solvates are also intended to be encompassed within the scope of this invention.

Some of the compounds of the general Formula (V) are already known.

Another object of the invention is the use of a compound of the general Formula (V):

het-(CH$_2$)$_n$—X-AB     (V)

where het is a five-membered or six-membered N-heteroaryl or a fused five-membered or six-membered N-heteroaryl;

n is an integer and is 0 or 1;

X is O, S, NR$_7$ and R$_7$ is selected from R$_3$;

and where the N-atom of the N-heteroaryl moiety and the —(CH$_2$)$_n$—X group are separated by one carbon atom;

R$_3$ is hydrogen; alkyl; cycloalkyl; aryl; aralkyl; alkenyl; cycloalkenyl; alkynyl; alkyl, cycloalkyl, aryl, aralkyl, alkenyl, cycloalkenyl, alkynyl containing one or more elements selected from the group consisting of O, S, N, halogen (F, Cl, Br, I);

A is aryl or heteroaryl;

B is a moiety containing a five-membered ring, wherein said ring is fused with A;

or a pharmaceutically acceptable salt or solvate thereof, or a solvate of such a salt; for the manufacture of a pharmaceutical product, which inhibits NAD(P)H oxidases (NOX) and the platelet activation or NAD(P)H oxidases (NOX) or the platelet activation.

Preferably, AB is the 1,2,3-triazolo[4,5-d]pyrimidine-7-yl radical of the general Formula (II):

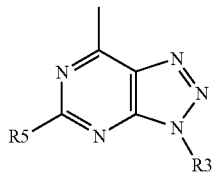

(II)

R$_3$ is hydrogen; alkyl; cycloalkyl; aryl; aralkyl; alkenyl; cycloalkenyl; alkynyl; alkyl, cycloalkyl, aryl, aralkyl, alkenyl, cycloalkenyl, alkynyl containing one or more elements selected from the group consisting of O, S, N, halogen (F, Cl, Br, I); and R$_5$ is hydrogen; halogen (F, Cl, Br, I); OH; R$_3$—S; R$_3$—O; NR$_1$R$_2$, where R$_1$ and R$_2$ are independently from each other R$_3$, or where R$_1$ and R$_2$ form together a ring system; het-(CH$_2$)$_n$—X.

The terms used in the Examples describing the invention are commonly used and known to those skilled in the art.

EXAMPLES

A. Preparation of 7-heteroarylthio-1,2,3-triazolo[4,5-d]pyrimidine derivatives and 7-heteroarylthio-(C-5-substituted)-1,2,3-triazolo[4,5-d]pyrimidine derivatives 1. Preparation of Starting Material of the General Formula (III)
2-mercaptothiazole A mixture of 2-bromothiazole (4.6 g, 28 mmol) and thiourea (6.4 g, 84 mmol) in 250 mL of methanol was heated under reflux for 2 h. The solution was evaporated and the residue stirred with 0.5N NaOH solution for 15 min. The solution was then acidified (pH 4) using acetic acid and extracted with ethyl acetate. The combined organic layers were washed with water and brine, dried (Na$_2$SO$_4$) and evaporated. After evaporation of the solvent, the product (0.6 g, 18% yield) was precipitated from ethylacetate and petrol ether.

$^1$H nmr (DMSO-D6): δ 13.2 (s, 1H, SH); 7.3 (d, 1H, CH═); 7.0 (d, 1H, CH═); ms: (+ACPI) m/z 118 (M+H)$^+$.
2-mercaptooxazole To a suspension of potassium thiocyanate (5.8 g, 60 mmol) in acetonitrile (150 mL) concentrated hydrochloric acid (6.2 g) was added dropwise under stirring. After stirring the suspension at room temperature for 1 h, the precipitated crystals were removed by filtration. To the obtained solution of thiocyanic acid in acetonitrile, glycolaldehyde dimer (2.4 g, 20 mmol) was added and refluxed for 4 h. After cooling, the solvent was evaporated and the residue was purified by chromatography (EA/EP=3/2) to obtain the product as solid beige (3.2 g, 98% yield). $^1$H nmr (DMSO-D6): δ 13.0 (s, 1H, SH); 7.7 (d, 1H, CH═); 7.3 (d, 1H, CH═); ms: (+ACPI) m/z 102 (M+H)$^+$.

2. Preparation of Starting Material for the Manufacture of Compounds of the General Formula (IV)
Benzylazide A mixture of sodium azide (7.6 g, 116.9 mmol), benzyl bromide (10 g, 58.4 mmol) in DMSO (80 mL) was stirred at room temperature for 18 h. The reaction mixture was then slowly poured into ice water and extracted with ether (3×200 mL). The combined organic extracts were washed with water and brine, dried (Na$_2$SO$_4$) and evaporated, giving the title compound as a colourless oil (6.9 g, 88% yield).

$^1$H nmr (DMSO-D6): δ 4.25 (s, 2H, CH$_2$), 7.2-7.4 (m, 5H, Ph). ms: (+EI) m/z 133 [M]$^+$.
4-amino-3-benzyl-5-aminoacetyl-triazole Cyanoacetamide (4.34 g, 51.6 mmol) and benzyl azide (6.87 g, 51.6 mmol) were sequentially added to a solution of sodium ethoxide (3.51 g, 51.6 mmol) in ethanol (50 mL). The reaction mixture was refluxed for 4 h. The solid was filtered and washed with water, dried on a dessiccator over P$_2$O$_5$, giving the title compound as a white solid (7.8 g, 70% yield).

$^1$H nmr (DMSO-D6): δ 4.35 (br s, 2H, NH$_2$), 5.35 (s, 2H, CH$_2$), 7.2-7.4 (m, 5H, Ph), 7.5 (s, 2H, CONH$_2$). ms: (+APCI) m/z 218 [M+H]$^+$.
General Method for the Preparation of 3-benzyl-7-hydroxy-1,2,3-triazolo[4,5-d]pyrimidines 4-amino-3-benzyl-5-aminoacetyl-triazole (0.5 g, 2.3 mmol) and ethyl formiate (ethyl acetate for 5-Me or ethyl benzoate for 5-Ph) (9.2 mmol) were added to a solution of sodium ethoxide (0.78 g, 11.5 mmol) in ethanol (50 mL). The mixture was refluxed for 24 h, the solvent evaporated and water added. The white solid formed was filtered and washed with water, corresponding to the title compound (0.38 g, 73% yield).
3-benzyl-7-hydroxy-1,2,3-triazolo[4,5-d]pyrimidine $^1$H nmr (DMSO-D6): δ 5.55 (s, 2H, CH$_2$), 7.2-7.3 (m, 5H, Ph), 7.9 (s, 1H, H-5), 12.8 (s, 1H, OH). ms: (+APCI) m/z 228 [M+H]$^+$.
3-benzyl-7-hydroxy-5-methyl-1,2,3-triazolo[4,5-d]pyrimidine $^1$H nmr (DMSO-D6): δ 2.4 (s, 3H, Me), 5.7 (s, 2H, CH$_2$), 7.3-7.4 (m, 5H, Ph). ms: (+APCI) m/z 242 [M+H]$^+$.
3-benzyl-7-hydroxy-5-phenyl-1,2,3-triazolo[4,5-d]pyrimidine $^1$H nmr (DMSO-D6): δ 5.6 (s, 2H, CH$_2$), 7.2-7.3 and 7.8-7.9 (m, 10H, Ph). ms: (+APCI) m/z 304 [M+H]$^+$.
3. General Procedure for the Preparation of 3-benzyl-7-chloro-1,2,3-triazolo[4,5-d]pyrimidines of the Formula (IV)

To a suspension of the appropriate 3-benzyl-7-hydroxy-triazolopyrimidine (5-H, Me or Ph) (10.56 mmol) in chloroform (50 mL), DMF (2 mL) and thionyl chloride (9 mL) were added and the mixture was refluxed for 3 h. The solvent was evaporated keeping the temperature below 35° C. The crude was chromatographed on silica gel eluting with petrol ether-ethyl acetate mixtures. The white solid obtained corresponds to the title compound (1.14 g, 44%).
3-benzyl-7-chloro-1,2,3-triazolo[4,5-d]pyrimidine (Starting Compound 1)

$^1$H nmr (DMSO-D6): δ 6.00 (s, 2H, CH$_2$), 7.3-7.4 (m, 5H, Ph), 9.1 (s, 1H, H-5). ms: (+APCI) m/z 246 [M+H]$^+$.
3-benzyl-7-chloro-5-methyl-1,2,3-triazolo[4,5-d]pyrimidine (Starting Compound 2)

$^1$H nmr (DMSO-D6): δ 2.8 (s, 3H, Me), 5.9 (s, 2H, CH$_2$), 7.3-7.4 (m, 5H, Ph). ms: (+APCI) m/z 260 [M+H]$^+$.
3-benzyl-7-chloro-5-phenyl-1,23-triazolo[4,5-d]pyrimidine (Starting Compound 3):

$^1$H nmr (DMSO-D6): δ 6.0 (s, 2H, CH$_2$), 7.3-7.4 (m, 3H, Ph), 7.5 (m, 2H, Ph), 7.6 (m, 3H, Ph), 8.5 (m, 2H, Ph). ms: (+APCI) m/z 322 [M+H]$^+$.
4. General Procedure for the Preparation of 7-heteroarylthio-1,2,3-triazolo[4,5-d]pyrimidine derivatives and 7-heteroarylthio-(C-5-substituted)-1,2,3-triazolo[4,5-d]pyrimidines Derivatives of the General Formula (I)

A solution of 3-benzyl-7-chloro-triazolopyrimidine (0.2 g, 1 eq.) of the Formula (IV), the appropriate compound of the Formula (III) (1 eq.) and triethylamine (1 eq.) in ethanol (5 mL) was stirred at room temperature or refluxed for 5 h. The mixture was diluted with DCM, washed with NaHCO$_3$ sat. and brine, dried (Na$_2$SO$_4$) and evaporated. Purification by column chromatography gave the title compounds.

Example 1

Compound of Formula (III): 2-mercapto-benzoxazole
Compound of Formula (IV): starting compound 1
3-benzyl-7-(2-benzoxazolyl)thio-1,2,3-triazolo[4,5-d]pyrimidine (74% yield)
$^1$H nmr (DMSO-D6): δ 5.85 (s, 2H, CH$_2$), 7.3-7.4 (m, 5H, Ph), 7.5-7.6 (m, 2H, Ar), 7.85 (d, 1H, Ar), 7.95 (d, 1H, Ar), 8.95 (s, 1H, H-5). ms: (+APCI) m/z 361 [M+H]$^+$.

Example 2

Compound of Formula (III): 2-mercapto-pyridine
Compound of Formula (IV): Starting Compound 1
3-benzyl-7-(2-pyridyl)thio-1,2,3-triazolo-[4,5-d]pyrimidine (53% yield)
$^1$H nmr (DMSO-D6): δ 5.90 (s, 2H, CH$_2$), 7.3-7.4 (m, 5H, Ph), 7.55 (m, 1H, Pyr), 8.0 (d, 2H, Pyr), 8.7 (d, 2H, Pyr), 8.9 (s, 1H, H-5). ms: (+APCI) m/z 321 [M+H]$^+$.

Example 3

Compound of Formula (III): 2-mercapto-oxazole
Compound of Formula (IV): Starting compound 1
3-benzyl-7-(2-oxazolyl)thio-1,2,3-triazolo[4,5-d]pyrimidine (73% yield)
$^1$H nmr (DMSO-D6): δ 5.90 (s, 2H, CH$_2$), 7.3-7.4 (m, 5H, Ph), 7.6 (s, 1H, Ar), 8.55 (s, 1H, Ar), 8.95 (s, 1H, H-5). ms: (+APCI) m/z 311 [M+H]$^+$.

Example 4

Compound of Formula (III): 2-mercapto-thiazole
Compound of Formula (IV): starting compound 1
3-benzyl-7-(2-thiazolyl)thio-1,2,3-triazolo[4,5-d]pyrimidine (83% yield)
$^1$H nmr (DMSO-D6): δ 6.1 (s, 2H, CH$_2$), 7.4-7.5 (m, 5H, Ph), 8.2 (d, 1H, Ar), 8.3 (d, 1H, Ar), 9.15 (s, 1H, H-5). ms: (+APCI) m/z 327 [M+H]$^+$.

Example 5

Compound of Formula (III): 2-mercapto-imidazole
Compound of Formula (IV): starting compound 1
3-benzyl-7-(2-imidazolyl)thio-1,2,3-triazolo[4,5-d]pyrimidine (74% yield)
$^1$H nmr (DMSO-D6): δ 5.8 (s, 2H, CH$_2$), 7.1 (s, 1H, Imid), 7.2-7.3 (m, 5H, Ph), 7.4 (s, 1H, Imid), 8.8 (s, 1H, H-5). ms: (+APCI) m/z 310 [M+H]$^+$.

Example 6

Compound of Formula (III): 2-mercapto-benzoxazole
Compound of Formula (IV): Starting compound 2
3-benzyl-7-(2-benzoxazolyl)thio-5-methyl-1,2,3-triazolo[4,5-d]pyrimidine (63% yield)
$^1$H nmr (DMSO-D6): δ 2.7 (s, 3H, Me), 5.85 (s, 2H, CH$_2$), 7.3-7.4 (m, 5H, Ph), 7.5-7.6 (m, 2H, Ar), 7.85 (d, 1H, Ar), 7.95 (d, 1H, Ar). ms: (+APCI) m/z 375 [M+H]$^+$.

Example 7

Compound of Formula (III): 2-mercapto-benzoxazole
Compound of Formula (IV): starting compound 3
3-benzyl-7-(2-benzoxazolyl)thio-5-phenyl-1,2,3-triazolo[4,5-d]pyrimidine (62% yield)
$^1$H nmr (DMSO-D6): δ 5.9 (s, 2H, CH$_2$), 7.3-7.6 (m, 10H, Ar), 7.9 (d, 1H, Ar), 8.0 (d, 1H, Ar), 8.15 (d, 2H, Ar). ms: (+APCI) m/z 437 [M+H]$^+$.

B. Preparation of 7-heteroarylthio-(N-3-substituted)-triazolopyrimidine derivatives 1. Preparation of starting material for the preparation of 7-chloro-(N-3-substituted)-1,2,3-triazolo[4,5-d]pyrimidines derivatives of the Formula (IV)
4,6-dichloro-5-nitropyrimidine Dimethylaniline (32.6 mL, 246 mmol) was added to a suspension of 4,6-dihydroxy-5-nitropyrimidine (25 g, 160 mmol) in phosphorus oxychloride (96 mL, 1056 mmol) and heated in an oil-bath at 125-130° C. for 1 h. The excess of phosphorus oxychloride was removed by evaporation and the residue was poured on ice (300 g). The solid formed was filtrated and the filtrated was extracted with ether. The combined organic layers were washed with water and brine, dried (Na$_2$SO$_4$) and evaporated. After evaporation of the solvent, the residue was purified by short chromatography in DCM and the product was obtained as pale brown solid (21.5 g, 70% yield).

$^1$H nmr (DMSO-D6): δ 8.3 (s, 1H, Ar).

General Procedure for the Synthesis of 4-chloro-6-aminosubstituted-5-nitro pyrimidine Compounds The appropriate amine (0.8-0.9 eq.) was added portionwise to a stirred solution of 4,6-dichloro-5-nitropyrimidine (31 mmol, 1 eq.) and triethylamine (2 eq.) in THF (100 mL) at 0° C. The resulting solution was stirred between 0° C. and room temperature for 2 h. Water was then added and the mixture of reaction was extracted with ethylacetate.

The combined organic layers were washed with water and brine, dried (Na$_2$SO$_4$) and evaporated. After evaporation of the solvent, the residue was purified by chromatography (PE/EA) to obtain the desired product.

4-chloro-6-methylamino-5-nitropyrimidine (56% yield):
$^1$H nmr (DMSO-D6): δ 8.4 (s, 1H, Ar); 8.3 (br s, 1H, NH); 2.9 (d, 3H, CH$_3$); ms: (+ACPI) m/z 189 (M+H)$^+$.

4-chloro-5-nitro-6-phenylaminopyrimidine (52% yield):
$^1$H nmr (DMSO-D6): δ 10.1 (s, 1H, NH); 8.4 (s, 1H, Ar); 7.5 (d, 2H, Ar); 7.4 (t, 2H, Ar); 7.2 (m, 1H, Ar); ms: (+ACPI) m/z 251 (M+H)$^+$.

4-chloro-6-p-methoxybenzylamino-5-nitropyrimidine (72% yield):
$^1$H nmr (DMSO-D6): δ 9.0 (broad t, 1H, NH); 8.4 (s, 1H, Ar); 7.2 (d, 2H, Ar); 6.9 (d, 2H, Ar); 4.6 (d, 2H, CH$_2$); 3.7 (s, 3H, CH$_3$); ms: (+ACPI) m/z 295 (M+H)$^+$.

4-chloro-6-o-chlorobenzylamino-5-nitropyrimidine (67% yield):
$^1$H nmr (DMSO-D6): δ 9.0 (br t, 1H, NH); 8.4 (s, 1H, Ar); 7.5 (m, 1H, Ar); 7.2 (m, 3H, Ar); 4.7 (d, 2H, CH$_2$); ms: (+ACPI) m/z 299 (M+H)$^+$.

General Procedure for the Synthesis of 4-chloro-6-aminosubstituted-5-amino pyrimidine Compounds Iron powder (10 eq.) was added to a very well stirred solution of the appropriate 4-aminosubstituted-6-chloro-5-nitro pyrimidine (14 mmol, 1 eq.) in acetic acid (300 mL) used as a solvent. The mixture was stirred at room temperature for 3 h and concentrated in vacuum. The residue was diluted with ethylacetate and the mixture washed with NaHCO$_3$ solution until pH neutral.

The combined organic layers were washed with water and brine, dried (Na$_2$SO$_4$) and evaporated to afford the title compound.

5-amino-4-chloro-6-methylaminopyrimidine (65% yield):

$^1$H nmr (DMSO-D6): δ 7.7 (s, 1H, Ar); 6.8 (br s, 1H, NH); 4.9 (s, 2H, NH$_2$); 2.9 (d, 3H, CH$_3$); ms: (+ACPI) m/z 159 (M+H)$^+$.

5-amino-4-chloro-6-phenylaminopyrimidine (91% yield):

$^1$H nmr (DMSO-D6): δ 8.6 (s, 1H, NH); 7.8 (s, 1H, Ar); 7.8 (d, 2H, Ar); 7.2 (t, 2H, Ar); 7.0 (m, 1H, Ar); 5.4 (s, 2H, NH$_2$); ms: (+ACPI) m/z 221 (M+H)$^+$.

5-amino-4-chloro-6-p-methoxybenzylaminopyrimidine (98% yield):

$^1$H nmr (DMSO-D6): δ 7.8 (s, 1H, NH); 7.2 (m, 3H, Ar); 6.9 (d, 2H, Ar); 5.1 (s, 2H, NH$_2$); 4.5 (d, 2H, CH$_2$); 3.7 (s, 3H, CH$_3$); ms: (+ACPI) m/z 265 (M+H)$^+$.

5-amino-4-chloro-6-o-chlorobenzylaminopyrimidine (67% yield):

$^1$H nmr (DMSO-D6): δ 7.7 (s, 1H, Ar); 7.4 (br s, 1H, NH); 7.2 (m, 4H, Ar); 5.1 (br s, 2H, NH$_2$); 4.6 (d, 2H, CH$_2$); ms: (+ACPI) m/z 269 (M+H)$^+$.

General Procedure for the Synthesis of 7-chloro-3-substituted-1,2,3-triazolo[4,5-d]pyrimidines as Starting Compounds of the Formula (IV) for the Preparation of 7-heteroarylthio-(N-3-substituted)-1,2,3-triazolo[4,5-d]pyrimidines Derivatives of the General Formula (I)

A solution of sodium nitrite (1.2 eq.) in water (30 mL) was added dropwise to a cold (0-5° C.) stirred solution of the appropriate 5-amino-4-chloro-6-aminoderivative pyrimidine (14 mmol, 1 eq.) in acetic acid (25 mL) and water (90 mL). The mixture was stirred for 2 h between 0° C. and room temperature. Ethylacetate was then added and the mixture was washed using NaHCO$_3$ solution until pH neutral. The combined organic layers were washed with water and brine, dried (Na$_2$SO$_4$) and evaporated to afford the title compound.

7-chloro-3-methyl-1,2,3-triazolo[4,5-d]pyrimidine (86% yield; starting compound 4)

$^1$H nmr (DMSO-D6): δ 9.1 (s, 1H, Ar); 4.4 (d, 3H, CH$_3$); ms: (+ACPI) m/z 170 (M+H)$^+$.

7-chloro-3-phenyl-1,2,3-triazolo[4,5-d]pyrimidine (96% yield; starting compound 5)

$^1$H nmr (DMSO-D6): δ 9.2 (s, 1H, Ar); 8.1 (m, 2H, Ar); 7.7 (m, 2H, Ar); 7.6 (m, 1H, Ar); ms: (+ACPI) m/z 232 (M+H)$^+$.

7-chloro-3-p-methoxybenzyl-1,2,3-triazolo[4,5-d]pyrimidine (82% yield: starting compound 6):

$^1$H nmr (DMSO-D6): δ 9.2 (s, 1H, Ar); 7.4 (d, 2H, Ar); 6.9 (d, 2H, Ar); 5.8 (s, 2H, CH$_2$); 3.7 (s, 3H, CH$_3$); ms: (+ACPI) m/z 276 (M+H)$^+$.

7-chloro-3-o-chlorobenzyl-1,2,3-triazolo[4,5-d]pyrimidine (96% yield; starting compound 7):

$^1$H nmr (DMSO-D6): δ 9.1 (s, 1H, Ar); 7.5 (m, 1H, Ar); 7.3 (m, 3H, Ar); 6.2 (s, 2H, CH$_2$); ms: (+ACPI) m/z 280 (M+H)$^+$.

2. General Procedure for the Synthesis of 7-heteroarylthio-(N-3-substituted)-1,2,3-triazolo[4,5-d]pyrimidine Derivatives of the General Formula (I)

2-mercapto-benzoxazole (1 eq.) was added to a solution of the appropriate 7-chloro-3-substituted-1,2,3-triazolo[4,5-d] pyrimidine (2 mmol, 1 eq.) and triethylamine (1.2 eq.) in EtOH (25 mL) at room temperature. The solution was stirred for 4 h. The precipitate was filtered and the filtrate purified via chromatography.

Example 8

Starting compound of Formula (III): 2-mercapto-benzoxazole

Starting compound of Formula (IV): starting compound 4

7-(2-benzoxazolyl)thio-3-methyl-1,2,3-triazolo[4,5-d]pyrimidine (51% yield by precipitation)

$^1$H nmr (DMSO-d$_6$): δ 9.0 (s, 1H, Ar); 7.9 (m, 1H, Ar); 7.8 (m, 1H, Ar); 7.4 (m, 2H, Ar); 4.3 (s, 3H, CH$_3$); ms: (+ACPI) m/z 284 (M+H)$^+$.

Example 9

Starting Compound of Formula (III): 2-mercapto-benzoxazole

Starting Compound of Formula (IV): Starting Compound 5

7-(2-benzoxazolyl)thio-3-phenyl-1,2,3-triazolo[4,5-d]pyrimidine (69% yield by precipitation)

$^1$H nmr (DMSO-d$_6$): δ 9.0 (s, 1H, Ar); 8.2 (m, 2H, Ar); 7.9 (m, 1H, Ar); 7.8 (m, 1H, Ar); 7.6 (m, 2H, Ar); 7.5 (m, 3H, Ar); ms: (+ACPI) m/z 347 (M+H)$^+$.

Example 10

Starting compound of Formula (III): 2-mercapto-benzoxazole

Starting compound of Formula (IV): starting compound 6

7-(2-benzoxazolyl)thio-3-p-methoxybenzyl-1,2,3-triazolo[4,5-d]pyrimidine (70% yield by precipitation)

$^1$H nmr (DMSO-d$_6$): δ 9.0 (s, 1H, Ar); 7.9 (d, 1H, Ar); 7.8 (d, 1H, Ar); 7.5 (m, 2H, Ar); 7.3 (d, 2H, Ar); 6.9 (d, 2H, Ar); 5.8 (s, 2H, CH$_2$); 3.7 (s, 3H, OCH$_3$); ms: (+ACPI) m/z 391 (M+H)$^+$.

Example 11

Starting Compound of Formula (III): 2-mercapto-benzoxazole

Starting Compound of Formula (IV): Starting Compound 7

7-(2-benzoxazolyl)thio-3-o-chlorobenzyl-1,2,3-triazolo[4,5-d]pyrimidine (75% yield by precipitation)

$^1$H nmr (DMSO-d$_6$): δ 8.9 (s, 1H, Ar); 7.8 (d, 1H, Ar); 7.7 (d, 1H, Ar); 7.5 (m, 3H, Ar); 7.3 (m, 3H, Ar); 6.0 (s, 2H, CH$_2$); ms: (+ACPI) m/z 395 (M+H)$^+$.

Particularly preferred compounds of the invention include:

TABLE 1

| Example | het-(CH$_2$)$_n$—X | R$_3$ | R$_5$ |
|---|---|---|---|
| 1 | (2-benzoxazolyl)thio | benzyl | H |
| 2 | (2-pyridyl)thio | benzyl | H |
| 3 | (2-oxazolyl)thio | benzyl | H |
| 4 | (2-thiazolyl)thio | benzyl | H |
| 5 | (2-imidazolyl)thio | benzyl | H |
| 6 | (2-benzoxazolyl)thio | benzyl | methyl |
| 7 | (2-benzoxazolyl)thio | benzyl | phenyl |
| 8 | (2-benzoxazolyl)thio | methyl | H |
| 9 | (2-benzoxazolyl)thio | phenyl | H |
| 10 | (2-benzoxazolyl)thio | 3-p-methoxybenzyl | H |
| 11 | (2-benzoxazolyl)thio | 3-o-chlorobenzyl | H |

C. Inhibition of NAD(P)H Oxidases

Measurement of cytochrome C-reduction was used to assess the NOX-activity in HL-60 cells.

Cell Culture

The human acute myeloid leukemia cell line HL-60 (ECACC 98070106) was cultured in RPMI 1640 (Biochrom, Berlin, Germany) supplemented with 5% heat-inactivated calf serum, 2 mM glutamine (GLUTAMAX, Invitrogen, Karlsruhe, Germany), 100 U/ml penicillin (Sigma, Taufkirchen, Germany), and 100 μg/ml streptomycin (Sigma, Taufkirchen, Germany) at 37° C. under a humidified atmosphere of 5% $CO_2$. Cells were maintained at $0.1$–$2.0 \times 10^6$ cells/ml. To induce myeloid differentiation, the cells were seeded to a density of $0.5 \times 10^6$ cells/ml and cultivated for 6 days in medium containing 1.25% (v/v) dimethylsulfoxide (DMSO).

Assay of NOX activity

Differentiated HL-60 cells were re-suspended and then washed in 1× volume HBSS without phenol red (Invitrogen, Karlsruhe, Germany). $40 \times 10^6$ cells were then washed in 4 ml HBSS containing 100 μM Cytochrome C (from horse heart, Sigma, Taufkirchen, Germany). After centrifugation (10 min at 300×g) the cell pellet was resuspended in 9 ml HBSS containing 111 μM Cytochrome C (final conc. in the assay after addition of other solutions: approx. 100 μM). The same solution of HBSS/Cytochrome C was used as a blank.

1 μl/well of each compound solution to be tested for its ability to inhibit NOX was pipetted into a 96 well plate (Greiner, Frickenhausen, Germany). At least two rows (i.e. 16 wells) of the 96 well plate were left empty. If compounds were dissolved in DMSO, 1 μl DMSO was added to the empty wells. 90 μl/well of the cell suspension in HBSS/Cytochrome C was added to the compounds. For controls, 90 μl/well of the cells were pipetted into 12 empty wells. For the blank, 90 μl of HBSS/Cytochrome C solution without cells were added to 4 empty wells. 1 μl of 1 mM Diphenyleneiodonium chloride* (DPI, final conc. 10 μM; Alexis, Lausen, Switzerland) was added to 4 control wells. DPI was used as a control inhibitor.

$E_{550}$ and $E_{540}$ were measured once before stimulation of the cells on a micro-plate reader (Multiskan Spektrum, Thermo Electron Corporation, Dreieich, Germany). $E_{540}$ was the isosbestic point and used to normalize absorbance at 550 nm ($E_{550}/E_{540}$). For stimulation, 10 μl of 1 μM Phorbol 12-myristate 13-acetate** (PMA, final conc. 100 nM; Alexis, Lausen, Switzerland) was added to the cells. 4 wells containing control cells were omitted. 10 μl HBSS was added to these 4 wells as well as to the blank.

The plate was shaken for 10 sec in the micro-plate reader and then incubated at 37° C. under a humidified atmosphere of 5% $CO_2$. $E_{550}$ and $E_{540}$ were measured after 60 and 120 min.

For calculation, the absorbance at 550 nm was normalized to absorbance at the isosbestic point at 540 nm for each individual well. The mean of the four blank values was subtracted from each corrected value for each time point. NOX-activities were expressed as % of the activity in PMA-stimulated control cells. Residual activity of DPI-treated cells was usually <10%.

In some experiments, 100 U/ml superoxide dismutase (SOD; from bovine erythrocytes, EC1.15.1.1; Alexis, Lausen, Germany) was used as a control. The inhibition of the signal by SOD was >95%.

*DPI solution: 10 mM stock solution in DMSO was diluted 1:10 in HBSS. This solution was used for the assay.

**PMA solution: 10 mM stock solution in DMSO was first diluted 1:10 in DMSO and then 1:100 in HBSS. This solution was further diluted 1:10 in HBSS and used for the assay.

TABLE 2

$IC_{50}$ values of compounds listed in Table 1

| Example | $IC_{50}$ [μM] |
|---|---|
| 1 | 2 |
| 2 | 13 |
| 3 | 2 |
| 4 | 2 |
| 5 | 12 |
| 6 | 1 |
| 8 | 2 |
| 9 | 1 |
| 10 | 2 |
| 11 | 2 |

D. Inhibition of Thrombin-Induced Platelet Activation

Expression of P-Selectin on the surface of platelets was used as a marker of platelet activation.

All experiments were performed with washed platelets (PRP). Fresh venous blood from healthy volunteers (40 ml) was collected into 10 ml of 5-fold CCD-solution (7 mM citric acid, 100 mM trisodium citrate, 140 mM glucose, 15 mM EGTA as anti-coagulant, pH 6.5). Platelet rich plasma was prepared by centrifugation at 300 g for 20 min. The supernatant was collected and incubated for 10 min at room temperature. Platelets were pelleted from the supernatant by a second centrifugation step at 500 g for 20 min. The pellet was resuspended in 5 ml HEPES buffer (145 in M NaCl, 5 mM KCl, 1 in M MgCl2, 10 mM glucose, 10 mM HEPES, pH 7.4). Platelet concentration was adjusted to $3 \times 10^8$ platelets/ml with HEPES buffer.

Washed platelets (0.2 ml) were silenced for 1 h at room temperature in siliconised reaction tubes. After pre-incubation with compounds of example 1-11 for 1 min the washed platelets were stimulated for 2 min with thrombin receptor activating peptide (TRAP-6, BACHEM Biochemicals, Heidelberg, Germany).

As a positive control, 0.2 ml of washed platelets were pre-incubated with 10 μM of the NO-releasing compound sodium nitroprussid (SNP, Sigma, Deisenhofen).

After incubation, 20 μl of the sample was pipetted to 10 μl of FITC-labelled anti-CD62P antibody (DAKO, Glostrup, Denmark) and incubated for 15 min in the dark. After incubation the samples were diluted with 1.5 ml of phosphate buffered saline and immediately measured on a cytometer.

For background substraction, one sample was incubated with 10 μl of FITC-labelled un-specific mouse IgG1 (DAKO, Glostrup, Denmark).

For cytometry the Becton-Dickinson FACS-Calibur instrument (settings: FSC: E00; SSC: 337 V; FL-1:600 V) was used. For each measurement 20000 cells were analysed. Results were obtained as mean fluorescence intensity (MFI) calculated using the CellQuest program (Ver. 1.0; Becton-Dickinson).

Inhibition of platelet activation is given as percent reduction of TRAP-6 induced P-Selectin expression in the presence of 5 μmol/l of examples 1-11:

TABLE 3

| Inhibition of platelet activation | |
|---|---|
| Example | % Inhibition of activation |
| 1 | 49 |
| 2 | 34 |
| 3 | 55 |
| 4 | 45 |
| 5 | 21 |
| 6 | 39 |
| 8 | 38 |
| 9 | 44 |
| 10 | 60 |
| 11 | 80 |

The invention claimed is:

1. A compound of the Formula (I)

$$het\text{-}X\text{-}AB \quad (I)$$

where het is five-membered or six-membered N-heteroaryl or fused five-membered or six-membered N-heteroaryl, wherein N-heteroaryl is optionally substituted, wherein the five-membered heteroaryl is selected from the group of imidazolyl, oxazolyl, isoxazolyl, thiazolyl, oxadiazolyl, thiadiazolyl, tetrazolyl, oxatriazolyl, and thiatriazolyl, and wherein six-membered N-heteroaryl is selected from the group consisting of pyrimidinyl, pyrazinyl, pyridazinyl, 1,2,3-triazinyl, 1,2,4-triazinyl, and 1,3,5-triazinyl;

X is S;

and where the N-atom of the N-heteroaryl moiety and the —X group are separated by one carbon atom;

AB is the 1,2,3-triazolo[4,5-d]pyrimidine-7-yl radical of the Formula (II)

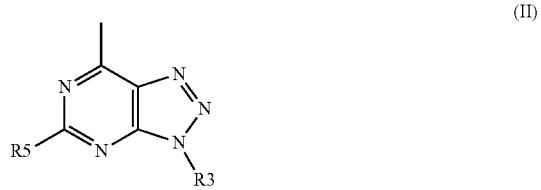

(II)

wherein AB is bound to X via the 4-position of the pyrimidine ring, wherein R3 is selected from the group consisting of hydrogen, alkyl, cycloalkyl, aryl, aralkyl, alkenyl, cyclo-alkenyl, and alkynyl, wherein at least one atom of alkyl, cycloalkyl, aryl, aralkyl, alkenyl, cyclo-alkenyl, or alkynyl is optionally substituted with one or more elements selected from the group consisting of O, S, N, F, Cl, Br, and I; and R5 is selected from the group consisting of hydrogen, $(C_1\text{-}C_8)$ alkyl, $(C_3\text{-}C_6)$ cycloalkyl, benzyl, phenyl, F, Cl, Br, I, OH, R4—S, R4—O, and $NR_1R_2$, wherein R4 is selected from the group consisting of hydrogen, alkyl, cycloalkyl, aryl, aralkyl, alkenyl, cyclo-alkenyl, and alkynyl, wherein at least one atom of alkyl, cycloalkyl, aryl, aralkyl, alkenyl, cyclo-alkenyl, or alkynyl is optionally substituted with one or more elements selected from the group consisting of O, S, N, F, Cl, Br, and I, and $R_1$ and $R_2$ are each independently selected from the group consisting of hydrogen, alkyl, cycloalkyl, aryl, aralkyl, alkenyl, cyclo-alkenyl, and alkynyl, wherein at least one atom of alkyl, cycloalkyl, aryl, aralkyl, alkenyl, cycloalkenyl, or alkynyl is optionally substituted with one or more elements selected from the group consisting of O, S, N, F, Cl, Br, and I, or where $R_1$ and $R_2$ form together a ring system;

or a pharmaceutically acceptable salt thereof.

2. The compound of claim 1, wherein N-heteroaryl is fused with an alicyclic, aromatic or heteroaromatic system.

3. The compound of claim 1, wherein one or more hydrogen atoms of the five-membered or six-membered N-heteroaryl or of the fused five-membered or six-membered N-heteroaryl are substituted independently from each other by one or more substituent selected from the group consisting of hydrogen, alkyl, cycloalkyl, aryl, aralkyl, alkenyl, cycloalkenyl, and alkynyl, wherein at least one atom of alkyl, cycloalkyl, aryl, aralkyl, alkenyl, cyclo-alkenyl, or alkynyl is optionally substituted with one or more elements selected from the group consisting of O, S, N, F, Cl, Br, and I.

4. The compound of claim 1, wherein het is five-membered N-heteroaryl, additionally comprising one O, S or N heteroatom, wherein the heteroaryl comprising an additional O atom may be precondensed to a benzene ring, or six-membered N-heteroaryl; wherein R3 is $C_{1\text{-}8}$ alkyl, phenyl or benzyl, optionally substituted with halogen or $C_{1\text{-}8}$ alkoxy group; and R5 is hydrogen, $C_{1\text{-}8}$ alkyl or phenyl.

5. The compound of claim 4, wherein the compound is 3-benzyl-7-(2-benzoxazolyl)thio-1,2,3-triazolo[4,5-d]pyrimidine.

6. A pharmaceutical composition comprising a carrier and a compound of claim 4.

* * * * *